(12) United States Patent
Gass et al.

(10) Patent No.: US 12,193,707 B2
(45) Date of Patent: *Jan. 14, 2025

(54) CONTINUOUS ANALYTE MONITOR INSERTER APPARATUS AND METHODS

(71) Applicant: Ascensia Diabetes Care Holdings AG, Basel (CH)

(72) Inventors: Jennifer L. Gass, Summit, NJ (US); Eugene Prais, West Milford, NJ (US); Thomas A. J. Mayer, Jr., Glenmoore, PA (US); Cameron M. Young, Tarrytown, NY (US); Nicholas Erekovcanski, Butler, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 34 days.

This patent is subject to a terminal disclaimer.

(21) Appl. No.: 18/331,774

(22) Filed: Jun. 8, 2023

(65) Prior Publication Data

US 2023/0310029 A1    Oct. 5, 2023

Related U.S. Application Data

(63) Continuation of application No. 16/984,107, filed on Aug. 3, 2020, now Pat. No. 11,707,297.

(Continued)

(51) Int. Cl.
*A61B 17/34*      (2006.01)
*A61B 5/00*       (2006.01)
(Continued)

(52) U.S. Cl.
CPC ........ *A61B 17/3468* (2013.01); *A61B 5/1451* (2013.01); *A61B 5/14532* (2013.01);
(Continued)

(58) Field of Classification Search
CPC .............. A61B 17/3468; A61B 5/1451; A61B 5/14532; A61B 17/3421; A61B 5/688;
(Continued)

(56) References Cited

U.S. PATENT DOCUMENTS 10,060,567 B2    8/2018  Van Nie et al.
2013/0274780 A1  10/2013 Trissel et al.
(Continued)

FOREIGN PATENT DOCUMENTS

CN         1822792 A    4/2010
CN       102238911 A   11/2011
(Continued)

OTHER PUBLICATIONS

Taiwan Patent Application 109128181 Official Letter issued Dec. 8, 2023.

(Continued)

*Primary Examiner* — David J. McCrosky
*Assistant Examiner* — Meghan R Kumar
(74) *Attorney, Agent, or Firm* — Erise IP, P.A.

(57) ABSTRACT

An apparatus for inserting a continuous analyte monitoring transmitter that includes an outer member, an inner member configured to telescope relative to the outer member, a transmitter, a bias member, an insertion device, and a pivot member. Force is applied to press the outer member toward an insertion site over the duration of a stroke. During a first portion of the stroke, the pivot member cannot pivot and the motion of the outer member translates to the insertion device until the biosensor is inserted at the insertion site. Over a second portion of the stroke, the continued motion causes a first pivot window in the outer member to overlap with a second pivot window in the inner member, allowing the pivot member to pivot and retract the insertion device from the insertion site, leaving the implanted biosensor. Upon (Continued)

completion of the stroke, the position of the pivot member is locked into place by engaging a locking feature of the bias member with the second pivot window to prevent the insertion member from re-entering the insertion site.

20 Claims, 15 Drawing Sheets

Related U.S. Application Data

(60) Provisional application No. 62/889,444, filed on Aug. 20, 2019.

(51) Int. Cl.
| | | |
|---|---|---|
| *A61B 5/145* | (2006.01) | |
| *A61B 17/00* | (2006.01) | |
| *B29C 53/02* | (2006.01) | |
| *B29L 31/00* | (2006.01) | |

(52) U.S. Cl.
CPC .......... *A61B 17/3421* (2013.01); *B29C 53/02* (2013.01); *A61B 5/688* (2013.01); *A61B 2017/00526* (2013.01); *A61B 2017/347* (2013.01); *A61B 2560/063* (2013.01); *B29L 2031/752* (2013.01); *B29L 2031/753* (2013.01)

(58) Field of Classification Search
CPC ...... A61B 2017/00526; A61B 217/347; A61B 2560/063; A61B 5/14503; B29C 53/02; B29L 2031/752; B29L 2031/753
See application file for complete search history.

(56) References Cited

U.S. PATENT DOCUMENTS

| | | |
|---|---|---|
| 2016/0331284 A1 | 11/2016 | Pace |
| 2017/0188912 A1* | 7/2017 | Halac ................ A61B 5/14532 |

FOREIGN PATENT DOCUMENTS

| | | |
|---|---|---|
| JP | 2019507613 A | 3/2019 |
| WO | 2019054113 A1 | 3/2019 |

OTHER PUBLICATIONS

Japanese Patent Application 2022-511080 Notice of Allowance issued Apr. 15, 2024.
Taiwan Patent Application 109128181 Notice of Allowance issued Aug. 6, 2024.

* cited by examiner

CONTINUOUS ANALYTE MONITOR INSERTER APPARATUS AND METHODS

RELATED APPLICATIONS

This application claims priority to U.S. patent application Ser. No. 16/984,107 entitled "CONTINUOUS ANALYTE MONITOR INSERTER APPARATUS AND METHODS" filed Aug. 3, 2020, which claims priority to U.S. Provisional Application Ser. No. 62/889,444 entitled "CONTINUOUS GLUCOSE MONITOR INSERTER APPARATUS AND METHODS" filed on Aug. 20, 2019, the disclosures of which are hereby incorporated by reference in their entirety herein.

FIELD

The present disclosure relates to inserters for continuous analyte monitoring, such as for use in continuous glucose monitoring (CGM).

BACKGROUND

Spinal CGM in an in-vivo sample has become a routine sensing operation, particularly in diabetes care. By providing real-time glucose concentrations, therapeutic actions such as insulin introduction may be applied in a timely manner such that a glycemic condition may be better controlled.

During CGM, a biosensor is typically inserted subcutaneously and continuously operated in an environment surrounded by tissue and interstitial fluid (ISF). The biosensor is inserted under the skin and provides a signal to a transmitter portion of the CGM system, and that signal is indicative of the patient's blood glucose level. These measurements may be made intermittently and automatically many times throughout the day (e.g., every few minutes or at some other interval) and transmitted to a receiving unit, typically wirelessly.

The transmitter portion of a CGM system is typically adhered to the outer surface of a user's skin, such as on the abdomen, on the back of the upper arm, or at another suitable location, while the biosensor is inserted through the skin so as to contact ISF. This skin insertion process may be referred to herein as "insertion." Devices for carrying out insertion may be referred to as "inserters" or "inserter apparatus" herein.

Inserter designs may be complicated and costly to manufacture. Accordingly, improved inserter methods and apparatus are desired.

SUMMARY

In some embodiments, a continuous analyte monitoring inserter apparatus is provided. The continuous analyte monitoring inserter apparatus includes an outer member; an inner member configured to telescope relative to the outer member; a transmitter carrier configured to support a transmitter and biosensor assembly, the transmitter carrier including a bias member; an insertion device; and a pivot member configured to pivot relative to the transmitter carrier and support the insertion device, wherein axial motion of the outer member is configured to press the bias member against the pivot member over a first portion of a stroke, and wherein the pivot member is prevented from pivoting over the first portion of a stroke thus facilitating movement of the transmitter carrier and the insertion device, and over a second portion of the stroke, the bias member is allowed to pivot the pivot member and retract the insertion device. The biosensor is inserted along with the insertion device during the first portion of the stroke. The insertion device is retracted in the second portion of the stroke leaving the implanted biosensor.

In some embodiments, an inserter configured to insert a biosensor of a transmitter and biosensor assembly includes an outer member having a first pivot window and a first alignment feature; an inner member having a second pivot window and a second alignment feature, wherein the inner member is configured to be telescopic within the outer member and the first alignment feature of the outer member is configured to interface with the second alignment feature of the inner member so as to vertically align the first pivot window with the second pivot window; a transmitter carrier configured to support a transmitter and biosensor assembly during insertion of a biosensor, the transmitter carrier including a bias member having an end feature; and a pivot member configured to pivot relative to the transmitter carrier, the pivot member including an insertion device support feature configured to support an insertion device during insertion and a bias member interface feature configured to couple with the end feature of the bias member. The outer member is configured to slide and translate relative to the inner member and press the bias member against the pivot member during insertion. Furthermore, during insertion, the pivot member is prevented from pivoting by the inner member until the insertion device inserts the biosensor of the transmitter and biosensor assembly into a subcutaneous region of a user and the first pivot window of the outer member overlaps with the second pivot window of the inner member and the pivot member enters the overlapping first and second pivot windows of the inner member and outer member, thereby allowing the bias member to pivot the pivot member and retract the insertion device from the subcutaneous region of the user.

In some embodiments, a method of forming an inserter apparatus includes providing an outer member; providing an inner member configured to telescope within the outer member; assembling an assembly of a transmitter carrier having a bias member, a pivot member, and an insertion device by placing the insertion device into an insertion device support feature of the pivot member and into a guide region of the transmitter carrier; and bending the bias member so that an end feature of the bias member contacts a bias member interface feature of the pivot member; and inserting the assembly into the outer member and the inner member.

In further embodiments, a method of using an inserter apparatus to insert a biosensor is provided. The method includes providing the inserter apparatus comprising: an outer member, an inner member, a transmitter carrier, a bias member coupled to the transmitter carrier, a pivot member configured to pivot relative to the transmitter carrier, and an insertion device including an insertion portion; providing a transmitter and biosensor assembly detachably coupled to the transmitter carrier; contacting an insertion site of a user's skin with the inner member; pushing on the outer member to cause the bias member to push against the pivot member thus causing the transmitter carrier and pivot member to move toward the insertion site, wherein the pivot member is prevented from pivoting over a first portion of a stroke of the inserter apparatus; continuing to move the transmitter carrier and pivot member toward the insertion site over the first portion of the stroke by further pushing with the bias member until the insertion portion of the insertion device makes contact with and enters the insertion site and contacts interstitial fluid, and a bottom surface of the transmitter and biosensor assembly contacts the skin; and performing a second portion of the stroke wherein the pivot member is allowed to pivot and the insertion portion of insertion device is retracted from the insertion site by the pivot of the pivot member pulling on the insertion portion.

Other features, aspects, and advantages of embodiments in accordance with the present disclosure will become more fully apparent from the following detailed description, the claims, and the accompanying drawings by illustrating a number of example embodiments and implementations. Various embodiments in accordance with the present disclosure may also be capable of other and different applications, and its several details may be modified in various respects, all without departing from the scope of the claims and their equivalents. Accordingly, the drawings and descriptions are to be regarded as illustrative in nature, and not as restrictive. The drawings are not necessarily drawn to scale.

BRIEF DESCRIPTION OF THE DRAWING FIGURES

DETAILED DESCRIPTION

In one or more embodiments described herein, an inserter apparatus, such as a continuous analyte (e.g., glucose) monitoring inserter apparatus, is provided that may be inexpensively manufactured, and in some embodiments, include one or more biodegradable and/or recyclable components. For example, in some embodiments, the inserter apparatus may include a transmitter carrier that holds a transmitter (e.g., a transmitter of a transmitter and biosensor assembly) during insertion of a biosensor of the assembly, and a bias member that biases the transmitter carrier toward a user during insertion. In one or more embodiments, the transmitter carrier and bias member may be formed from a single piece of material, which reduces manufacturing costs and complexity. The transmitter and biosensor assembly, once applied to the user's skin, can transmit signals to a receiving device (e.g., a receiver with a display or smartphone—not shown) wherein analyte measurements, such as continuous glucose measurements, may be received (e.g., wirelessly) and/or displayed.

In some embodiments, one or more portions of the inserter, such as those used to facilitate movement of the transmitter carrier toward a user during insertion, may be formed from a biodegradable and/or recyclable material (e.g., a recyclable plastic, a biodegradable paper product, etc.)

These and other features of the inserter, the manufacture of the inserter, and the use of the inserter to insert a biosensor into a user's skin are described below with reference to FIGS. 1A-8B herein.

Figure 1A:
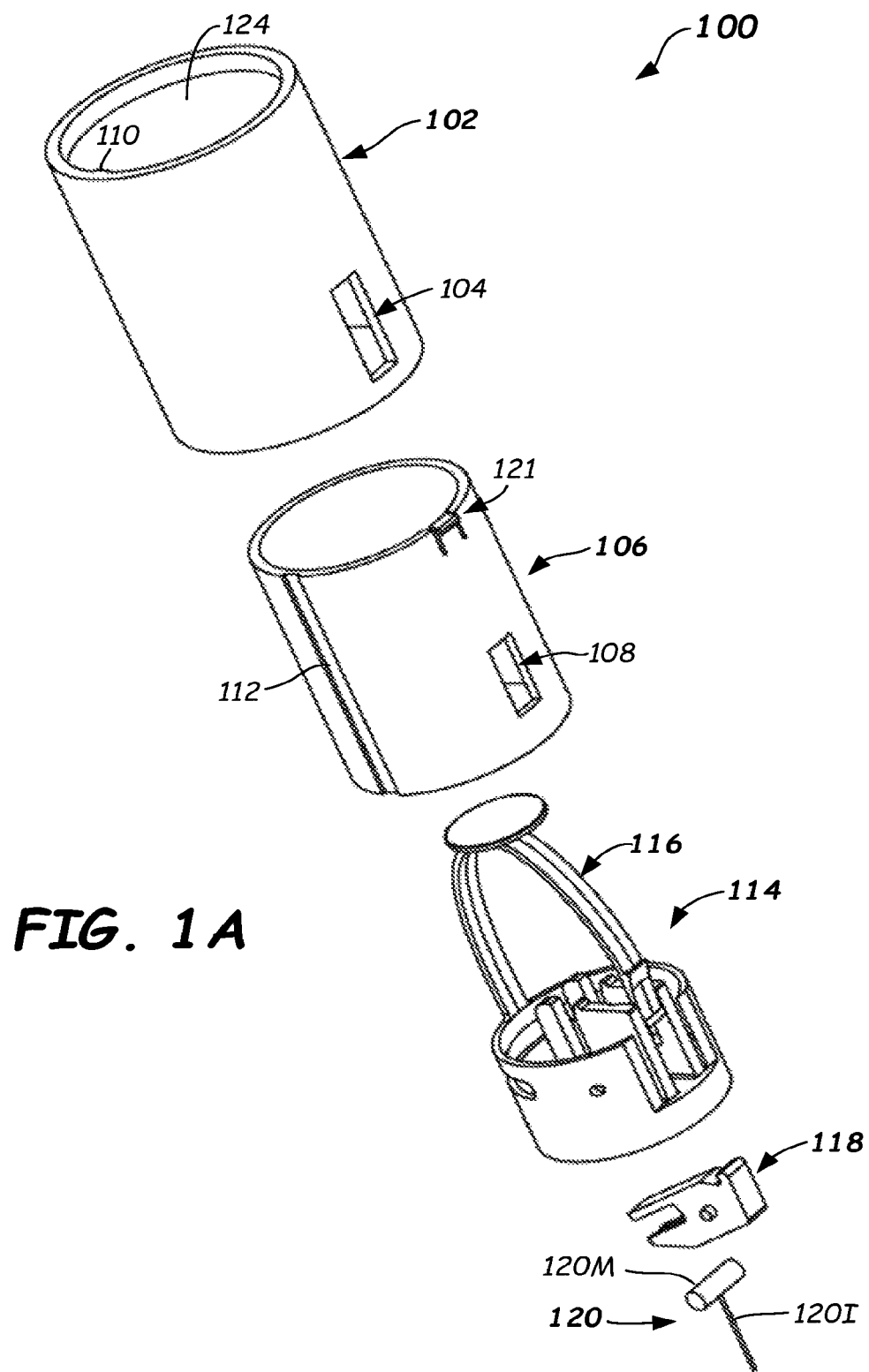
FIG. 1A is an exploded, side-perspective view of components of an example inserter apparatus (e.g., continuous analyte monitor (CAM) inserter apparatus) in accordance with one or more embodiments provided herein.

FIG. 1A is an exploded, side-perspective view of an example CGM inserter 100 in accordance with one or more embodiments provided herein. Although a CGM inserter 100 is shown, it should be apparent that the inserter apparatus described herein can be used for inserting other types of biosensors used in other types of continuous analyte monitoring systems, such as cholesterol, lactate, uric acid, alcohol, or other analyte monitoring systems, for example.

Again with reference to FIG. 1A, CGM inserter 100 may include an outer member 102, which may include a first pivot window 104 and an inner member 106 having a second pivot window 108. The term "window" as used herein means an opening in a sidewall. The opening can have a rectangular shape in side plan view, such as having four sides. However, in some embodiments, one or more of the first and second pivot windows 104, 108 may have only three sides. For example, one or more of the first and second pivot windows 104, 108 may open on their lower end, wherein the lower connecting portion or sill is removed. Other window shapes may be used (e.g., square, round, elliptical, etc.). In some embodiments, the outer member 102 and/or inner member 106 may be formed from a biodegradable and/or recyclable material (e.g., a recyclable plastic, a biodegradable paper product, bamboo, etc.). In other embodiments, outer member 102 and/or inner member 106 may be formed from one or more materials such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other materials may be used for outer member 102 and/or inner member 106.

As shown in FIG. 1A, inner member 106 may be configured to be concentric with outer member 102, and may be configured to be telescopic therein. Telescopic as used herein means that one element is capable of moving axially within another. In some embodiments, outer member 102 may include a first alignment feature 110, and inner member 106 may include a second alignment feature 112 that interfaces with the first alignment feature 110 of outer member 102. Such first and second alignment features 110, 112 may hold outer member 102 and inner member 106 in rotational alignment (e.g., prevent relative rotation of inner member 106 within outer member 102, such as during insertion) and constrain outer and inner members 102, 106 to telescopic motion. In one or more embodiments, first alignment feature 110 of outer member 102 may be configured to interface with the second alignment feature 112 of inner member 106 so as to vertically (and rotationally) align the first pivot window 104 of outer member 102 with the second pivot window 108 of inner member 106, as shown in FIG. 1A and FIGS. 3A-3F. In some embodiments, first and second alignment features 110, 112 may comprise a vertically aligned rib and groove, respectively. Outer member 102 and inner member 106 may include a cylindrical, oblong, oval, elliptical, or any other suitable outside surface shape in transverse cross-section. In some embodiments, outer member 102 and inner member 106 may not be concentric.

CGM inserter 100 may also include a transmitter carrier 114 configured to support a CGM transmitter and biosensor assembly 310 (FIGS. 3A-3F) during insertion of a biosensor 340 of the CGM transmitter and biosensor assembly 310. Transmitter carrier 114 may be sized to fit within inner member 106, and may include a bias member 116, that, in some embodiments, may be formed integrally therewith. Sized to fit means the transmitter carrier 114 is configured to be telescopic within the inner member 106, and may have a sliding fit therewith, for example. A slight interference fit may be provided between the transmitter carrier 114 and the inner member 106, so that the transmitter carrier 114 does not fall out of the inner member 106 due to gravity and so that relative motion is enabled by overcoming the friction.

CGM inserter 100 may further include a pivot member 118 that is configured to pivot, such as relative to the transmitter carrier 114, and support and operatively drive an insertion device 120 during the insertion method of the biosensor 340 of a CGM transmitter and biosensor assembly 310, as described further herein.

In some embodiments, transmitter carrier 114 and/or pivot member 118 may be formed from a plastic material such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other suitable materials may be used for transmitter carrier 114 and/or pivot member 118.

In some embodiments, inner member 106 may include a pre-insertion lock feature 121 configured to retain the inner member 106 relative to the outer member 102 until a certain applied design force (see FIG. 3A) is exceeded. After the design force F is exceeded, the inner member 106 may move further axially and translate (e.g., telescope) into the outer member 102. For example, pre-insertion lock feature 121 can be configured to extend into pivot window 104 of outer member 102, or another internal feature (e.g., lateral groove) of the outer member 102, so as to prevent outer member 102 from sliding further over inner member 106 prior to insertion, as described below with reference to FIGS. 3A-3F herein. However, after the design force is overcome through application of an axial force F by the user on the outer member 102, the pre-insertion lock feature 121 can flex and move axially inside and along the inner surface of the outer member 102 so that relative axial sliding (e.g., telescopic) motion of the inner member 106 into the outer member 102 is allowed.

Figure 1B:
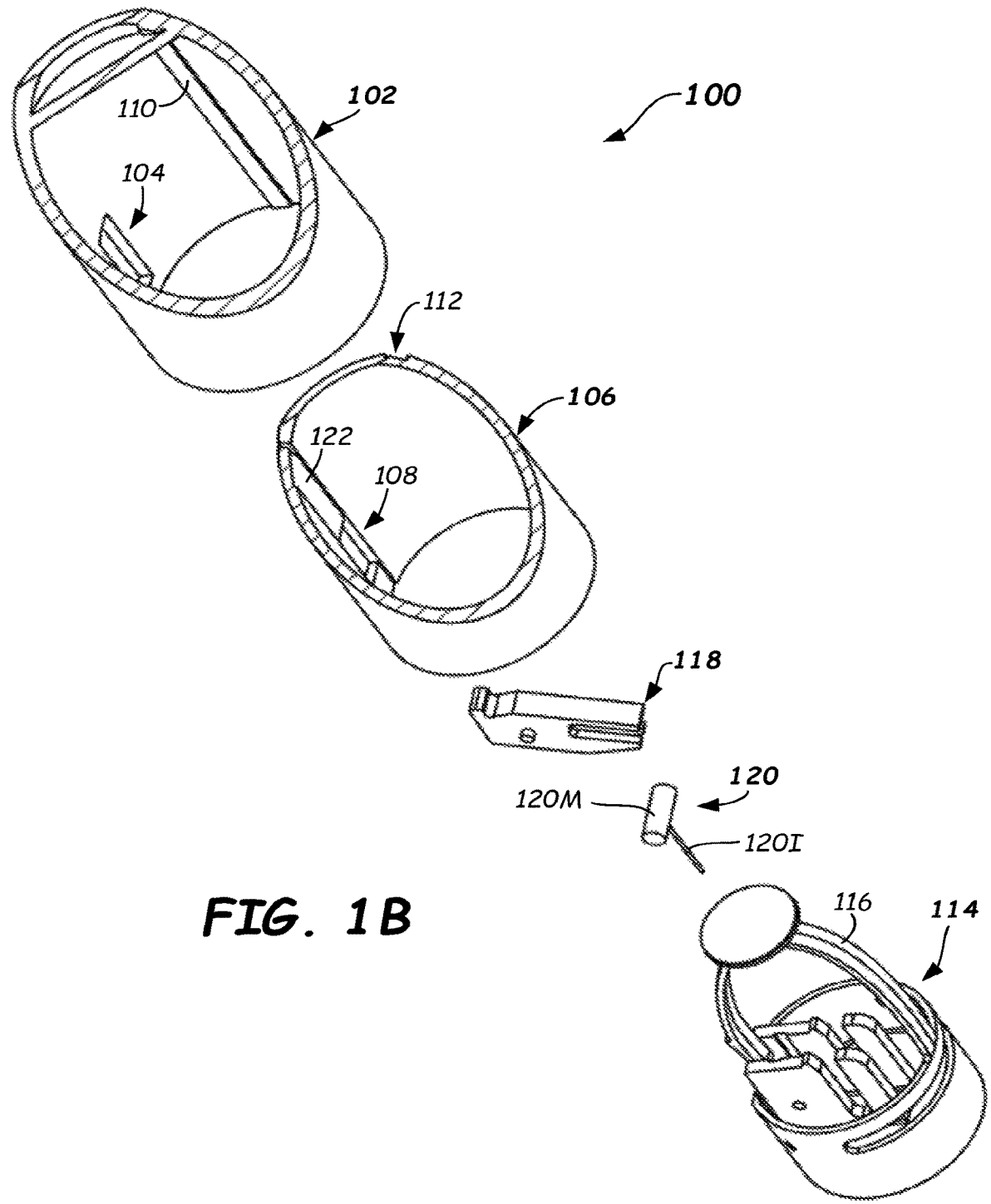
FIG. 1B is an exploded, side-perspective view of the example inserter of FIG. 1A, rotated by 180 degrees relative to FIG. 1A and with a portion of the outer member and the inner member removed for illustration purposes, in accordance with embodiments provided herein.

FIG. 1B is an exploded, side-perspective view of the example CGM inserter 100 of FIG. 1A, rotated by 180 degrees relative to FIG. 1A and with a portion of outer member 102 and inner member 106 removed for illustrative purposes, in accordance with embodiments provided herein. FIG. 1B illustrates an internal guide feature 122 of inner member 106 along which pivot member 118 may axially slide during at least part of a stroke during the insertion method, as described further herein. In some embodiments, internal guide feature 122 may be an axially disposed and aligned slot or groove, which may have a slightly larger width than the pivot member 118.

Figure 1C:
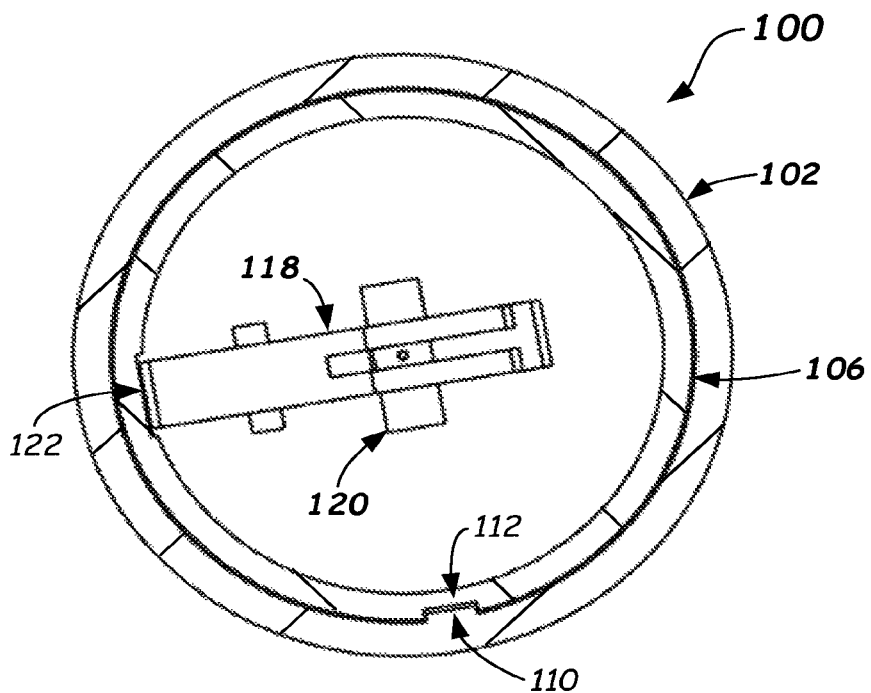
FIG. 1C is a cross-sectioned top view of the inserter of FIGS. 1A and 1B as assembled, with a cover of an outer member and a transmitter carrier removed for illustration purposes, in accordance with embodiments provided herein.

FIG. 1C is a top cross-sectioned view of the CGM inserter 100 of FIGS. 1A and 1B as assembled, with a cover 124 (FIG. 1A) of outer member 102 and the transmitter carrier 114 removed for illustration purposes, in accordance with embodiments provided herein. As shown in FIG. 1C, outer member 102 and inner member 106 may be concentrically arranged. First alignment feature 110 of outer member 102 may align with second alignment feature 112 of inner member 106 and maintain rotational and/or vertical alignment of first pivot window 104 of outer member 102 relative to second pivot window 108 of inner member 106 (FIG. 1A). FIG. 1C also illustrates the position of pivot member 118 being guided within internal guide feature 122 of inner member 106. Internal guide feature 122 can comprise a groove, for example. Note that other types and/or numbers of alignment features and/or guide features may be used. For example, inner member 106 may have a protruding alignment feature for alignment with a recess or groove formed in the outer member 102. Moreover, internal guide feature 122 may be a protruding guide feature, such as a rib received in a groove formed in the pivot member 118 for providing axial guiding of the pivot member 118.

Figure 2A:
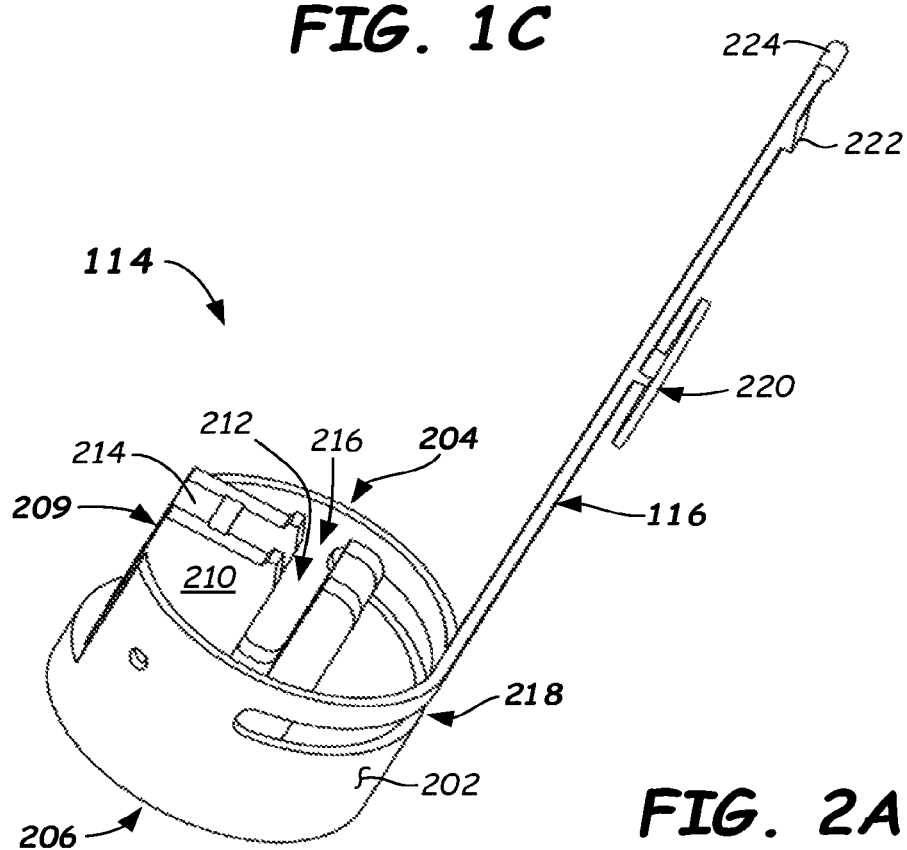
FIG. 2A is a side perspective view of an example embodiment of a transmitter carrier, with a bias member shown unbent, in accordance with embodiments provided herein.

FIG. 2A is a side perspective view of an example embodiment of transmitter carrier 114 with the coupled bias member 116 shown unbent, as provided herein. After manufacture and prior to assembly within CGM inserter 100, bias member 116 may be straight (or unbent) as shown in FIG. 2A.

With further reference to FIG. 2A, transmitter carrier 114 may be formed from a cylindrical body region 202 that includes an upper region 204 to which bias member 116 is coupled, and a lower region 206 which is used to support a CGM transmitter during insertion (as described further herein). Upper region 204 also houses supporting structure 209, which is configured to support the pivot member 118 (FIG. 1A). Supporting structure 209 may include a first side 210 having a first guide region 212 and a second side 214 having a second guide region 216. Guide regions 212 and 216 may comprise open-ended slots that can be axially oriented and extending and may be employed to axially guide the insertion device 120 (FIGS. 1A and 2D) during the insertion method, as described further herein.

Upper region 204 may have a compression feature 218 which may compensate for compression of soft tissue of the user during the insertion method. For example, during the insertion method, compression feature 218, which is a circumferentially extending slot in the depicted embodiment, may allow some movement of bias member 116 relative to lower region 206 of cylindrical body region 202 as the bottom of lower region 206 contacts the user's skin and compresses underlying soft tissue. This may facilitate maintaining the CGM transmitter and biosensor assembly 310 in contact with skin during the insertion method. Compression feature 218 alternatively may be located in lower region 206 or may be provided by another flexing structural configuration.

For example, in some embodiments compression feature 218 may include one or more openings in cylindrical body region 202. For example, a portion of cylindrical body region 202 may be removed as shown in FIG. 2A. In some embodiments, compression feature 218 may extend approximately half way around cylindrical body region 202, and may have a height of about 1 mm to 6 mm. Other types, numbers, locations and/or sizes of compression features may be used. In some embodiments, no compression feature may be employed.

Bias member 116 may include a contact feature 220 that may be configured to contact an underside of cover 124 (FIG. 1A) of outer member 102 during the insertion method. In some embodiments, contact feature 220 may be a flat region formed along a length of the bias member 116 that contacts the underside of cover 124 of outer member 102. Contact feature 220 may be a planar surface and may be round when viewed in a plan view. Other suitable shapes may be employed. Contact feature 220 may be secured to cover 124, or in other embodiments, merely come into contact with cover 124. For example, in some embodiments, contact feature 220 may be allowed to slide or otherwise move laterally relative to the underside of cover 124 as indicated by arrow 221 of FIG. 3A (e.g., contact feature 220 may form a sliding contact with cover 124). Contact feature 220 may facilitate substantially more uniform bending of bias member 116 during the insertion method, for example.

Bias member 116 may be formed from a flexible material, such as a flexible plastic, that allows bias member 116 to be curved or bent as shown in FIGS. 1A, 1B, 2C, and 3A-3F. Example dimensions of bias member 116 range from about 75 mm to 150 mm long, 3 mm to 8 mm wide, and 1.0 mm to 2.5 mm thick. Other dimensions may be used. Example bias member materials include acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other materials may be used.

As shown in FIG. 2A, in some embodiments, bias member 116 may include a locking feature 222 that may engage with second pivot window 108 of inner member 106 following insertion, so as to restrict movement of bias member 116, pivot member 118 and/or insertion device 120 following insertion (as described further herein). Bias member 116 may also include an end feature 224 for contacting pivot member 118. In some embodiments, end feature 224 may include a cylindrical portion adapted to mate with a like portion of the pivot member 118. However, other suitable end features enabling engagement with a feature of the pivot member 118 may be used.

Figure 2B:
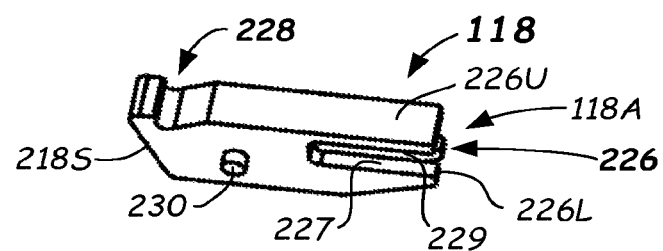
FIG. 2B is a side perspective view of an example embodiment of a pivot member in accordance with embodiments provided herein.

FIG. 2B is a side perspective view of an example embodiment of the pivot member 118, as provided herein. Pivot member 118 may include an insertion device support feature 226 on a first end 118A, such as a slot or other opening that is configured to support insertion device 120 during the insertion method. In particular, legs 120L (FIG. 2D) of the main body 120M of the insertion device 120 are supported during the first and second portions of the stroke, wherein the first portion comprises insertion of the insertion portion 1201 of the insertion device 120, and the second portion comprises retraction of the insertion portion 1201 of the insertion device 120 leaving the biosensor 240 implanted. Insertion device support feature 226 (FIG. 2B) may comprise a first extending slot 227, which may extend fully through the lateral width of the pivot member 118 and may have an open end on the first end 118A, thus forming a fork with upper fork member 226U and lower fork member 226L. Fork is configured and sized to slidably receive the main body portion 120M of the insertion device 120. A second extending slot 229 can extend vertically through the lower fork member 226L to intersect with the first extending slot 227 and can be configured and sized to receive the insertion portion 1201 of the insertion device 120 (See FIG. 2D). Upper and lower are used herein to refer to the orientation shown in FIG. 2B for illustration purposes, but it should be recognized that the pivot member 118 may be oriented in other orientations during its use.

Additionally, pivot member 118 may include a bias member interface feature 228 configured to interface with end feature 224 of the bias member 116. Pivot member 118 may also include one or more pivot features 230 that allow pivot member 118 to pivot relative to the transmitter carrier 114. For example, pivot member 118 may include pivot features 230 that comprise pivot posts (only one pivot post is shown in FIG. 2B) that interface with apertures in the first and second sides 210 and 214 of supporting structure 209 of the transmitter carrier 114 (see FIG. 2C). Openings 231 may be opposed slots, which allow some defined axial motion of the pivot member 118 during the assembly via pivot posts sliding in openings 231 and coming to rest in pivot openings 232 (FIG. 2C) formed in the respective first and second sides 210 and 214. Other suitable pivot mechanisms may be used.

Figure 2C:
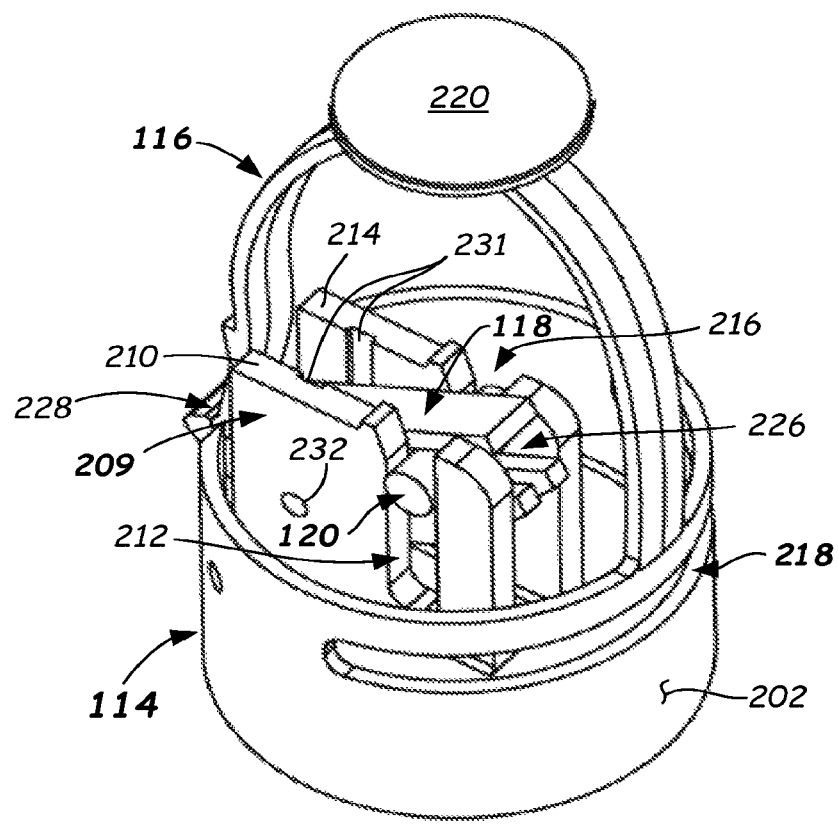
FIG. 2C is a side perspective view of a transmitter carrier assembled with a pivot member and an insertion device in accordance with embodiments provided herein.
Figure 2D:
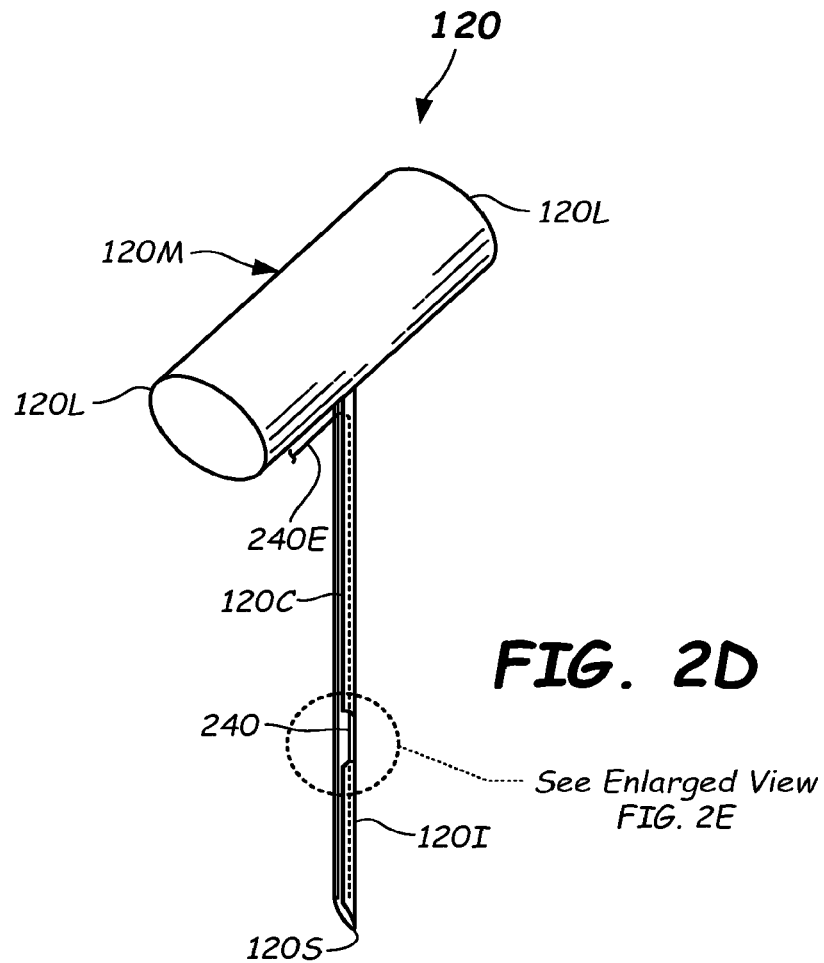
FIG. 2D is a side perspective view of an insertion device including a biosensor in accordance with embodiments provided herein.
Figure 2E:
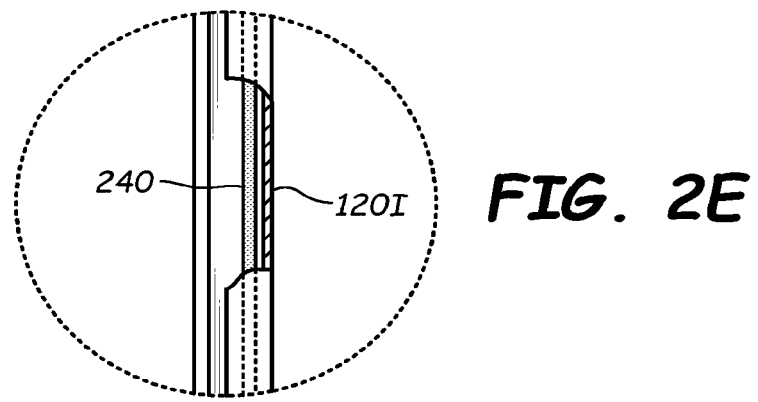
FIG. 2E is an enlarged break out view of a portion of an insertion device including a biosensor therein in accordance with embodiments provided herein.

FIG. 2C illustrates a side perspective view of transmitter carrier 114 assembled with pivot member 118 and insertion device 120, in accordance with embodiments provided herein. As shown in FIG. 2C, bias member 116 is bent or curved so that end feature 224 of bias member 116 contacts and registers in bias member interface feature 228 (see FIG. 3A). Pivot feature 230 (e.g., a post of FIG. 2B) of pivot member 118 can interface with and snap into pivot opening 232 of first side 210 of supporting structure 209. A similar pivot feature on the opposite side of pivot member 118 may interface with and snap into a like pivot opening formed in second side 214 of supporting structure 209 (not shown).

Main body 120M of insertion device 120 slides into insertion device support feature 226 of pivot member 118 (e.g., into the fork), and also into guide regions 212 and 216 (e.g., open ended slots) of first and second sides 210 and 214 of supporting structure 209. Insertion device 120 may be further supported during insertion by opening 306 formed in the transmitter carrier 114. For example insertion portion 1201 may slide in opening 306 during insertion.

Assembly and operation (the insertion method) of CGM inserter 100 are now described with reference to FIGS. 3A-3F, which illustrate side cross-sectional views of CGM inserter 100 during different portions of the stroke of the insertion method of a biosensor (e.g., CGM biosensor 240) in accordance with embodiments provided herein.

Figure 3A:
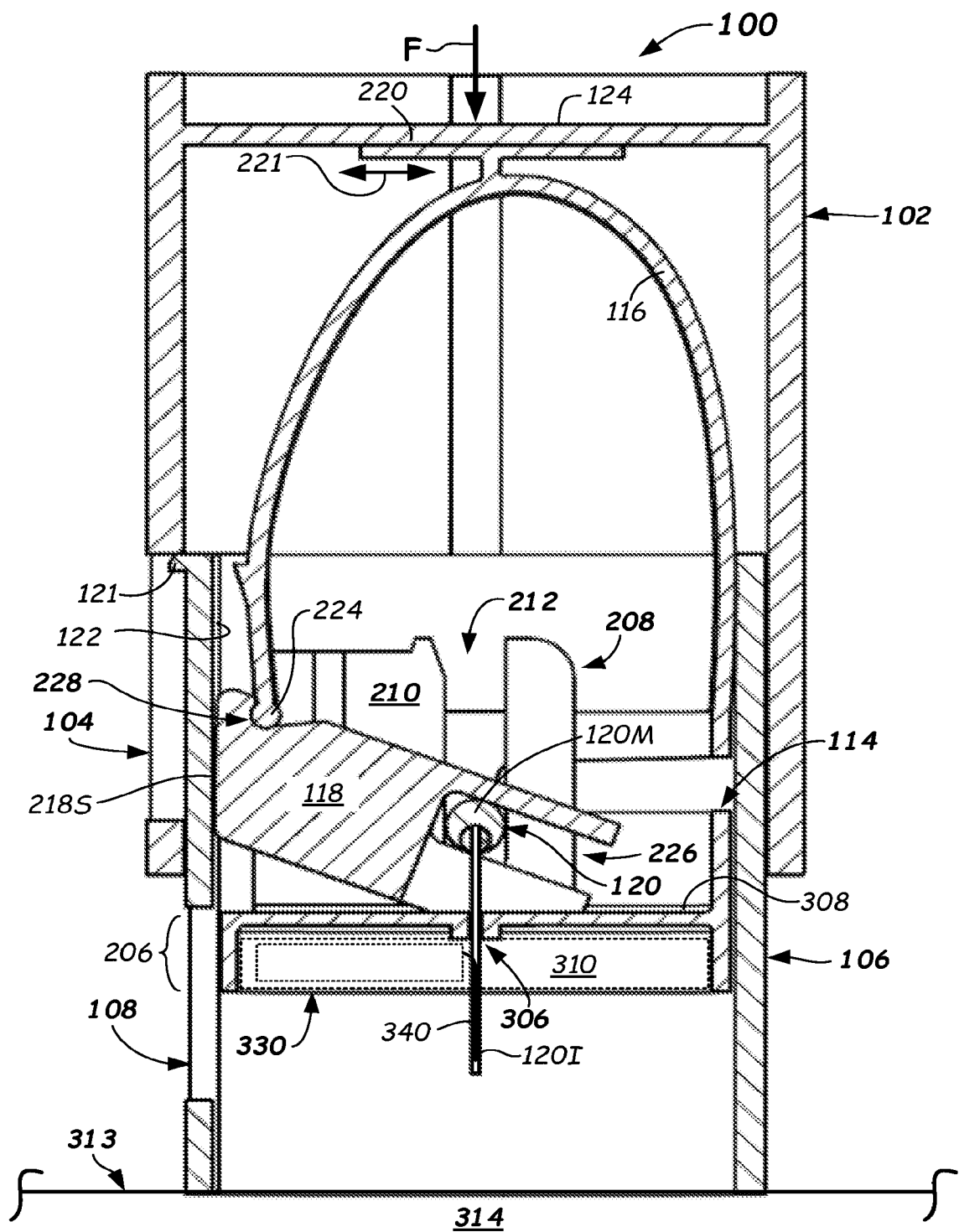
FIGS. 3A-3F illustrates side cross-sectional views of an inserter at various portions of a stroke during a method of insertion of a biosensor (e.g., a continuous analyte monitor (CAM) biosensor such as a CGM biosensor) in accordance with embodiments provided herein.

With reference to FIG. 3A, to assemble CGM inserter 100, insertion device 120 is placed into insertion device support feature 226 of pivot member 118, and also into guide regions 212 and 216 of first and second sides 210 and 214 of supporting structure 209. Bias member 116 is bent or curved so that end feature 224 of bias member 116 comes into contact and registers with bias member interface feature 228 of pivot member 118. Pivot feature 230 (FIG. 2B) is interfaced with pivot opening 232 (FIG. 2C) of first side 210 of supporting structure 209. A similar pivot feature on the opposite side of pivot member 118 may be interfaced with a pivot opening in second side 214 of supporting structure 209 (not shown).

As shown in FIG. 3A, insertion device 120 has a main body portion 120M that resides within insertion device support feature 226 (e.g., fork) of pivot member 118, and an insertion portion 1201 that is extendable into a lower region 206 of transmitter carrier 114 through the supporting opening 306 in a floor region 308 of transmitter carrier 114, and past the transmitter carrier 114 (for use during the insertion method) Insertion portion 1201 of insertion device 120 can have a sharpened end 120S (FIG. 2D) that pierces the user's skin 313 (FIGS. 3A-3F) to introduce a biosensor 240 (e.g., CGM biosensor) into a subcutaneous region of a user at an insertion site 314 as described further herein. Insertion portion 1201 also may be referred to as an insertion shaft, needle, trocar, sharp, or the like. Upon retraction of the insertion portion 1201, the biosensor 340 received in the insertion portion 1201 remains in the subcutaneous region of the user, i.e., is implanted therein.

In some embodiments, opening 306 in floor region 308 of transmitter carrier 114 is positioned and/or centered below guide regions 212 and 216 of first and second sides 210 and 214 of supporting structure 209 such that insertion portion 1201 is supported to remain approximately vertically oriented (as shown) during insertion (and/or approximately perpendicular to a region into which the insertion portion 1201 is to be inserted), as shown in FIG. 3A. Opening 306 may include a close fit with insertion portion 1201 so as to act as an alignment guide to provide the approximately perpendicular orientation thereof, for example.

Insertion portion 1201 of insertion device 120 may be made, for example, from a metal such as stainless steel, or a non-metal such as plastic. Other suitable materials may be used. In some embodiments, insertion portion 1201 of insertion device 120 may include an open-sided channel 120C extending along the length of the insertion portion 1201 that may be, but is not limited to, a round C-channel tube, a round U-channel tube, a stamped sheet metal part folded into a square U-profile, a molded/cast metal part with a square U-channel profile, or a solid metal cylinder with an etched or ground square U-channel. Other insertion portion shapes may be used that allow insertion and retraction while leaving the implanted biosensor 340 (e.g., CGM biosensor) behind. Upon retraction of the insertion portion 1201, biosensor 240 may slide along inside open-sided channel 120C and remain implanted, while the exiting portion 240E of the biosensor can slide along the opening of the open-sided channel 120C.

Main body portion 120M of insertion device 120 may include a cylindrical or other shaped body and may extend laterally as shown to the respective sides 210, 214 of supporting structure 209, and may be formed from a plastic material, for example, such as, but not limited to, acrylonitrile butadiene styrene (ABS), polycarbonate, nylon, acetal, polyphthalamide (PPA), polysulfone, polyethersulfone, polyetheretherketone (peek), polypropylene, high-density polyethylene (HDPE), and low-density polyethelene (LDPE). Other materials may be used.

[Following assembly of transmitter carrier 114 with pivot member 118 and insertion device 120, transmitter carrier 114 is inserted into outer member 102 and inner member 106. For example, contact feature 220 of transmitter carrier 114 may be coupled to cover 124 of outer member 102 (e.g., by an adhesive, a suitable snap-fit fastening mechanism, etc.). Cylindrical body region 202 may contact an inner surface of inner member 106, as may a portion of bias member 116 as shown. Bias member 116 also may contact outer member 102 (via contact feature 220) as described herein.

Thus, the method of forming an inserter apparatus 100 involves providing an outer member 102; providing an inner member 106 configured to telescope within the outer member 102; assembling an assembly (FIG. 2C) of a transmitter carrier 114 having a bias member 116, a pivot member 118, and an insertion device 120 by placing the insertion device 120 into an insertion device support feature 226 of the pivot member 118 and into a guide region of the transmitter carrier 114; bending the bias member 116 so that an end feature 224 of the bias member 116 contacts a bias member interface feature 228 of the pivot member 116; and inserting the assembly (FIG. 2C) into the outer member 102 and the inner member 106.

As shown in FIGS. 3A-3F, inner member 106 is sized to fit within outer member 102, i.e., is configured to be telescopic within the outer member 102, and may have a close sliding fit therewith, for example. In some embodiments, inner member 106 may include pre-insertion lock feature 121 that is configured to extend into the first pivot window 104 of outer member 102 so as to prevent outer member 102 from sliding over inner member 106 too far prior to insertion.

Upon application of sufficient axial force F applied to outer member 102, such as from the user, then surface 218S of pivot member 118 may move (e.g., vertically as shown) thus sliding relative to inner member 106 along guide feature 122 (e.g., a groove). In the position shown in FIG. 3A, pivot member 118 is prevented from pivoting by inner member 106 while pivot member 118 resides within guide feature 122. In particular, the pivot member 118 is prevented from pivoting over a first portion of a stroke of the CGM inserter 100.

In operation, a transmitter and biosensor assembly 310 (e.g., CGM transmitter and biosensor assembly—shown dotted) can be detachably coupled to the transmitter carrier 114. The transmitter and biosensor assembly 310 may be positioned within a recess 330 in the lower region 206 of transmitter carrier 114 in some embodiments. During the insertion, the insertion portion 1201 extends through transmitter and biosensor assembly 310. Transmitter and biosensor assembly 310 can include an adhesive layer (not shown) to adhere the transmitter and biosensor assembly 310 to the user's skin 313. However, as should be apparent, a recess is optional, and the transmitter and biosensor assembly 310 may be simply detachably mounted to the lower region 206 of the transmitter carrier 114 by any suitable releasable mechanism.

To begin the insertion method, inserter apparatus 100 is placed in contact with the skin 313 at an insertion site 314 of a user, such as on an upper arm, an abdomen region, or another suitably approved location to avoid insertion into muscle. This is shown in FIG. 3A.

To begin insertion, an axial force F is applied to the outer member 102 by the user (or other person) so as to cause the outer member 102 to slide over the inner member 106 and translate toward the insertion site 314. In some embodiments, the outer member 502 (FIG. 5) can include a top profile 503 comprising a non-planar top surface portion configured to be held by the user's (or other person's) hand, wherein the top profile 503 includes a compound curved surface including multiple continuous radii extending across the top profile 503.

Figure 3B:
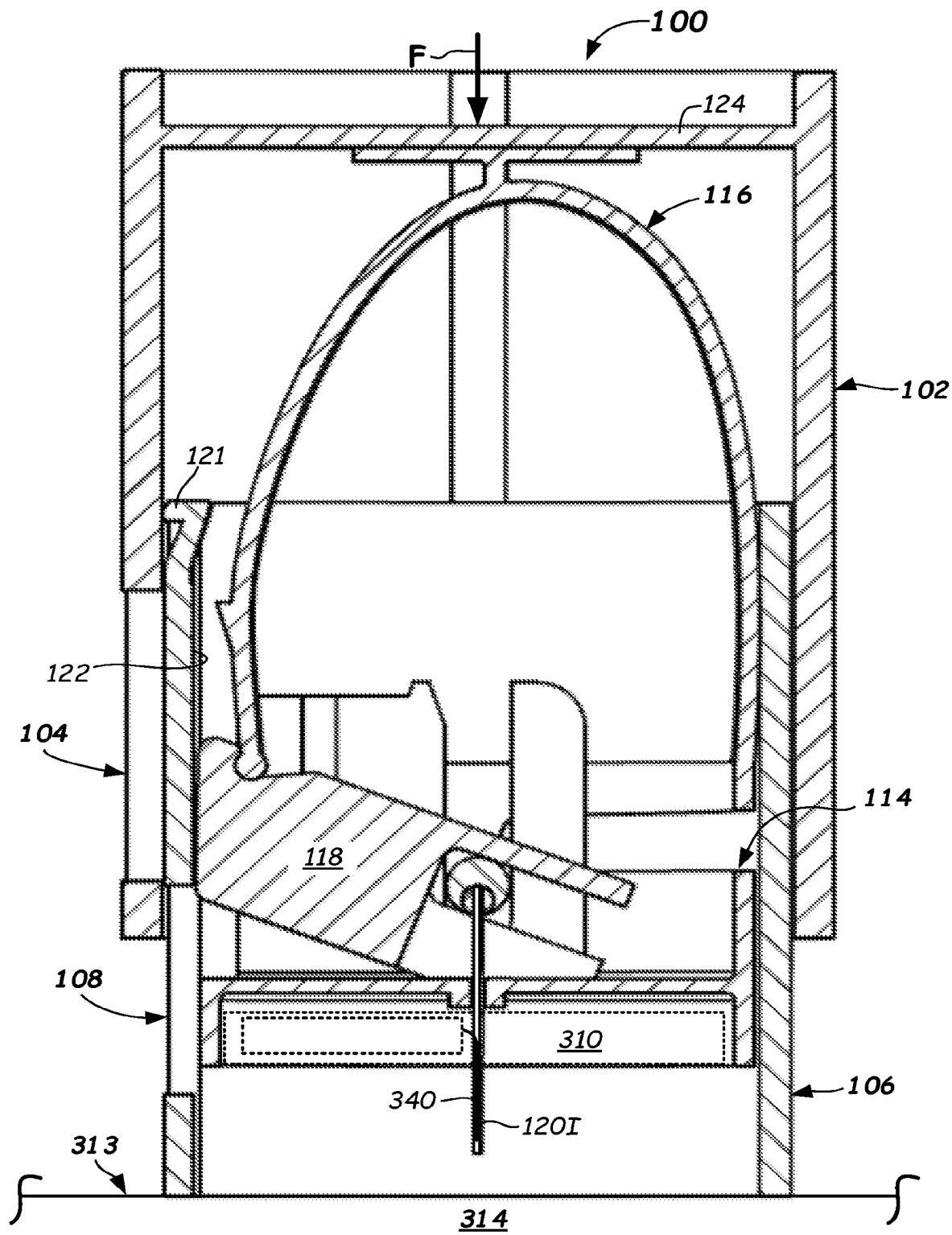

The top profile 503 and curvatures can be formed in an ergonomic shape to allow more effortless grasping and pushing to apply the axial force F as well as to remove the inserter apparatus 100. The top profile 503 can include at least convex curvatures 503CV, but may also include concave curvatures 503CC in some embodiments. Movement of outer member 102 (or outer member 502) over inner member 106 causes transmitter carrier 114 and pivot member 118 to move (e.g., translate) toward the insertion site 314, as shown in FIG. 3B. Force sufficient to cause pre-insertion lock feature 121 to flex inward and out of pivot window 104 of outer member 102 is applied to begin the first portion of the axial stroke of the insertion method. During this stage (first portion of the stroke) of the insertion method, pivot member 118 is prevented from pivoting via contact with inner member 106, as transmitter carrier 114 and pivot member 118 move (translate) toward the insertion site 314 along internal guide feature 122 of the inner member 106.

Figure 3C:
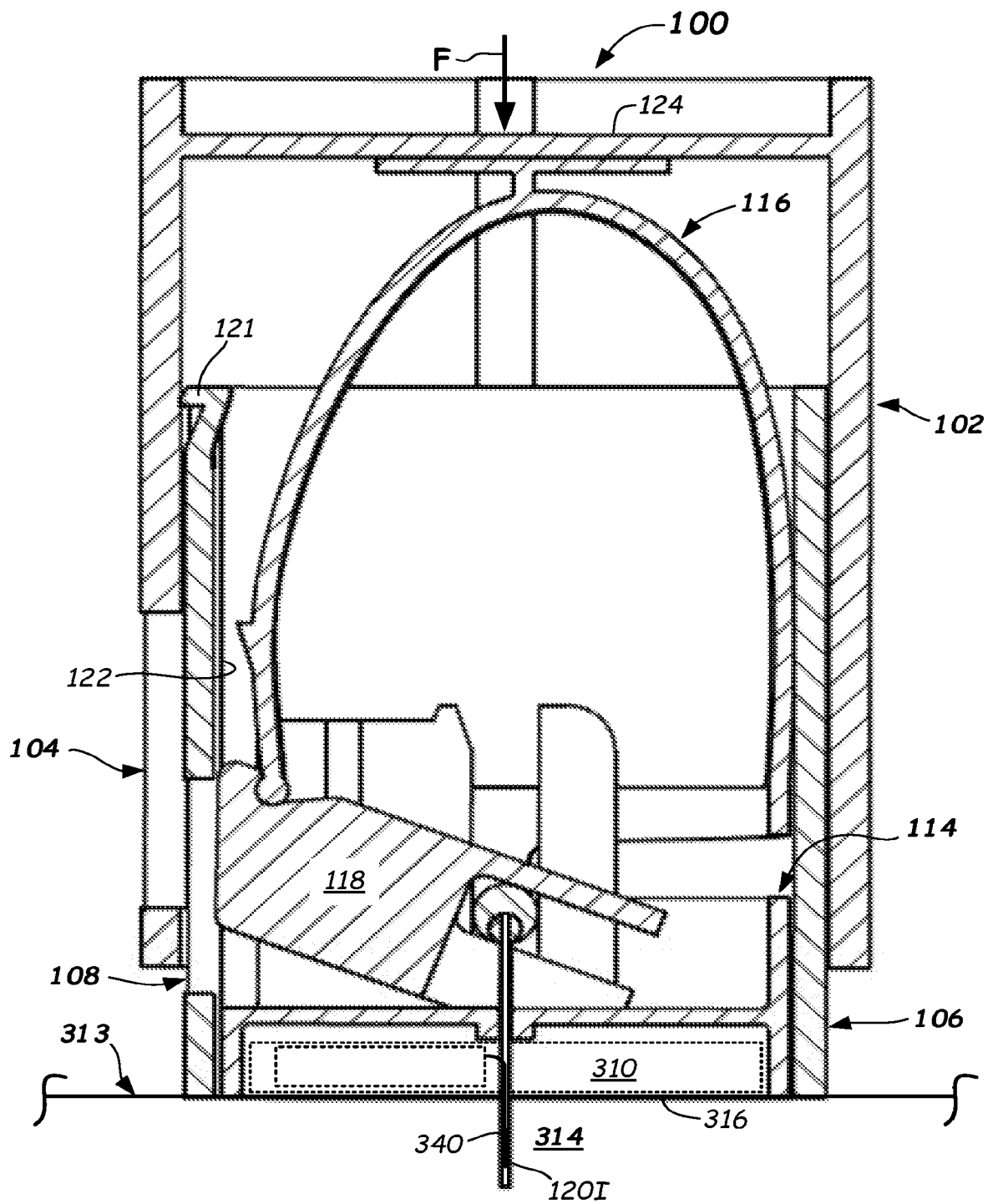

As shown in FIG. 3C, transmitter carrier 114 and pivot member 118 move toward the insertion site 314 until insertion portion 1201 makes contact and enters insertion site 314, and a bottom surface 316 of transmitter and biosensor assembly 310 contacts the skin 313 at the insertion site 314. In some embodiments, bottom surface 316 of transmitter and biosensor assembly 310 may include an adhesive material (e.g., a pressure sensitive adhesive) that adheres to the user's skin 313 at the insertion site 314 at this stage. A CGM biosensor 340 (FIG. 3D) enters the insertion site 314 with the insertion portion 1201 of insertion device 120 (where it will make contact with interstitial fluid).

As shown in FIG. 3C, pivot member 118 remains in contact with the inner surface of inner member 106 and is still prevented from pivoting at this stage. This causes insertion portion 1201 to remain in a fixed position relative to the pivot member 118 and transmitter carrier 114.

Figure 3D:
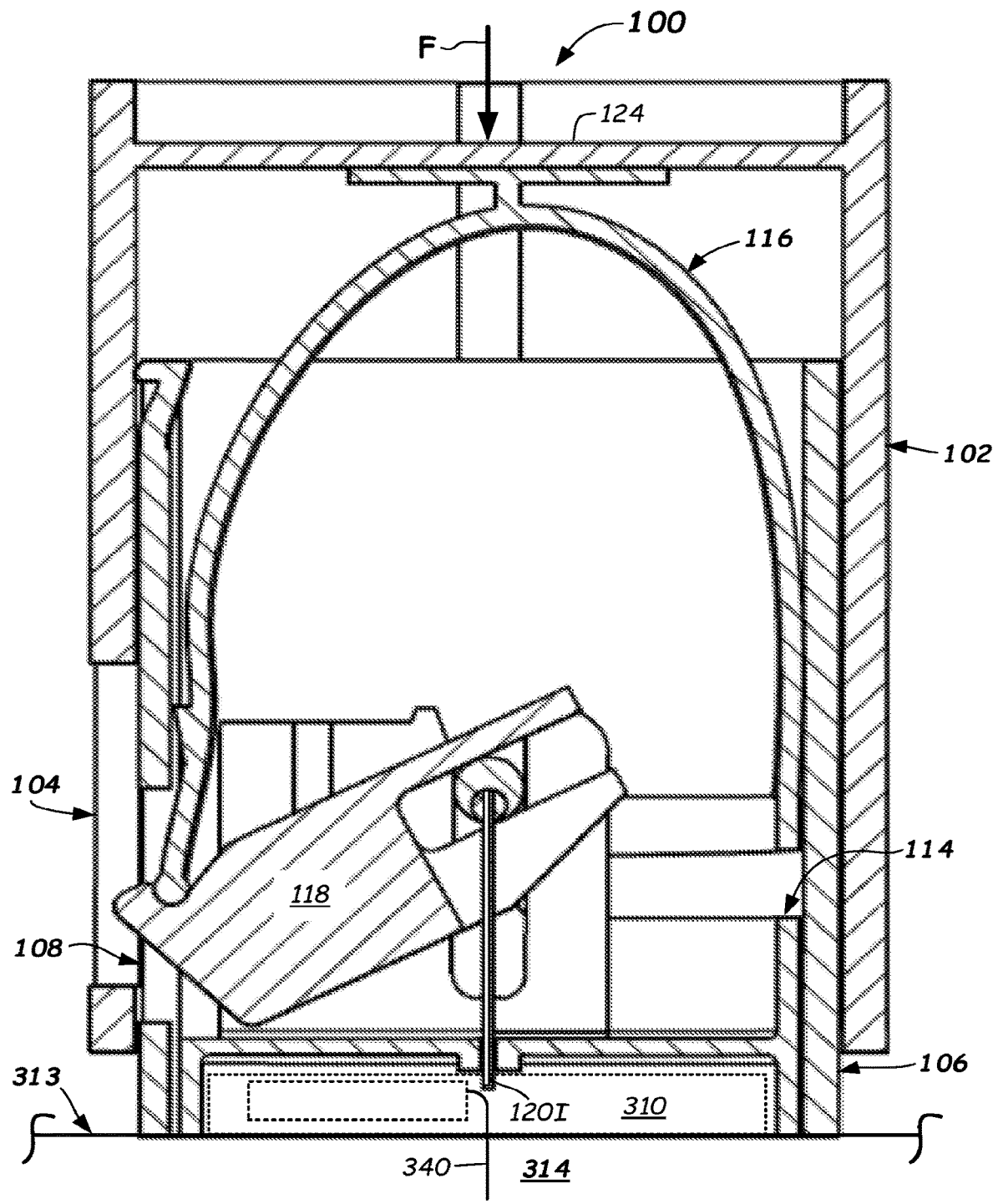

As shown in FIG. 3D, following insertion of the CGM biosensor 340 (and/or adhesion of the transmitter and biosensor assembly 310 to the insertion site 314), the outer member 102 continues to move axially and telescopically over the inner member 106 toward the insertion site 314. As the end of the pivot member 118 enters into the second pivot window 108 of the inner member 106, the pivot member 118 is now free to start to pivot in the second portion of the stroke. Upon further push motion, the end of the pivot member 118 can enter into the overlapping first and second pivot windows 104, 108 of the outer and inner members 102, 106. First pivot window 104 of the outer member 102 then overlaps with second pivot window 108 of the inner member 106 such that pivot member 118 is now free to fully pivot by entering the overlapping first and second pivot windows 104, 108 of the outer and inner members 102, 106. Pivot member 118 pivots due to the force applied by bias member 116 on pivot member 118 (as shown in FIG. 3D). As this occurs, insertion portion 1201 of insertion device 120 retracts from the insertion site 314 during the second portion of the stroke. In at least one embodiment, a height of second pivot window 108 of inner member 106 and/or a height of first pivot window 104 of outer member 102 may be selected so as to specify and/or dictate when pivot member 118 starts to pivot and/or fully pivots during the insertion method.

Figure 3E:
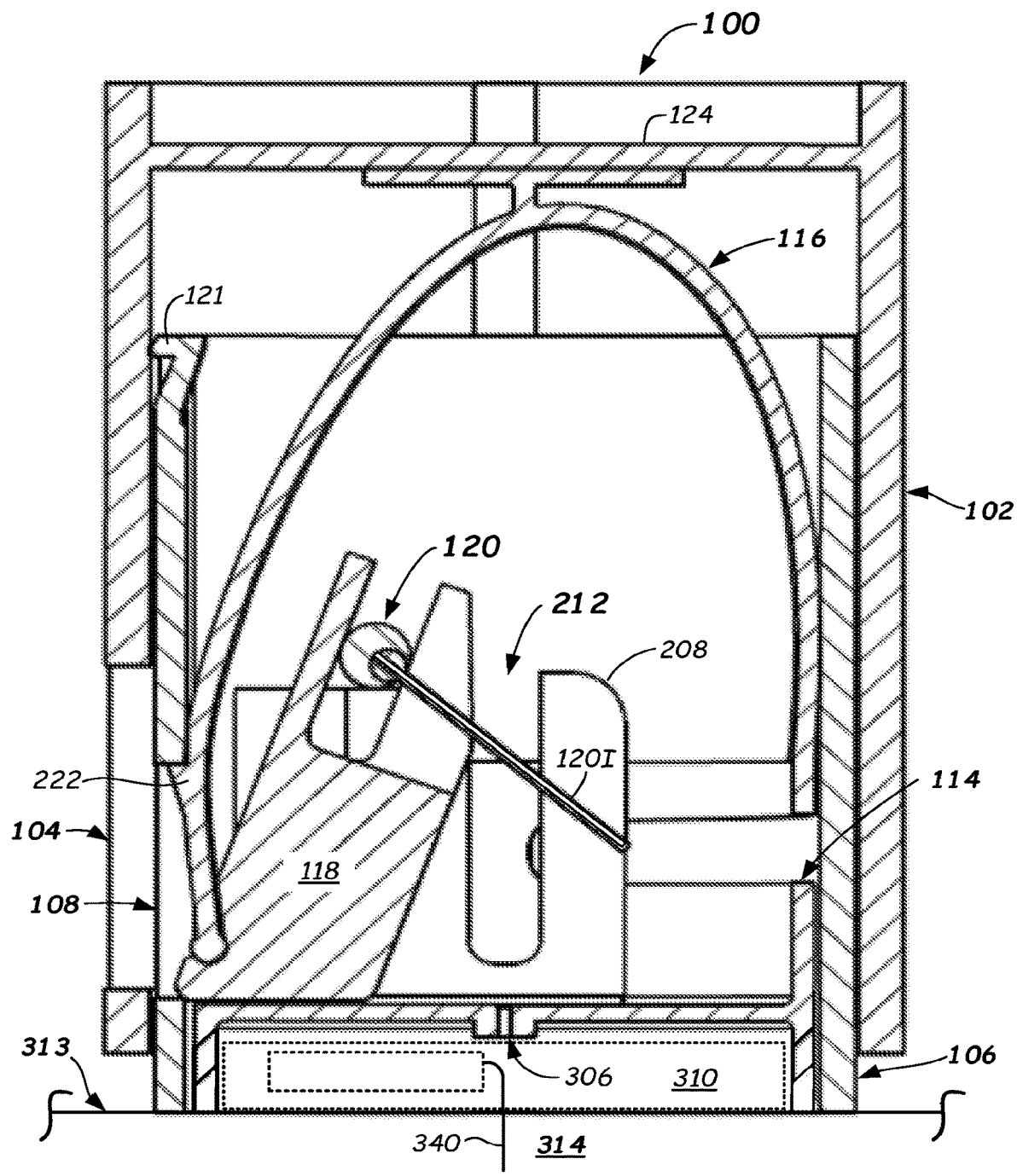

As the outer member 102 continues to move over the inner member 106 toward the insertion site 314, cover 124 of outer member 102 continues to push bias member 116 against pivot member 118. Eventually, as shown in FIG. 3E, pivot member 118 pivots enough for insertion device 120 to entirely exit and leave the opening 306, and may also leave the guide region 212 of support structure 209 of transmitter carrier 114. As such, insertion portion 1201 of insertion device 120 cannot inadvertently be reinserted into insertion site 314. Additionally, as bias member 116 continues to move toward insertion site 314, after insertion, locking feature 222 of bias member 116 can enter into second pivot window 108 of the inner member 106. This prevents bias member 116 from retracting (and pivot member 118 from pivoting in a direction that might cause insertion device 120 to re-enter insertion site 314).

Figure 3F:
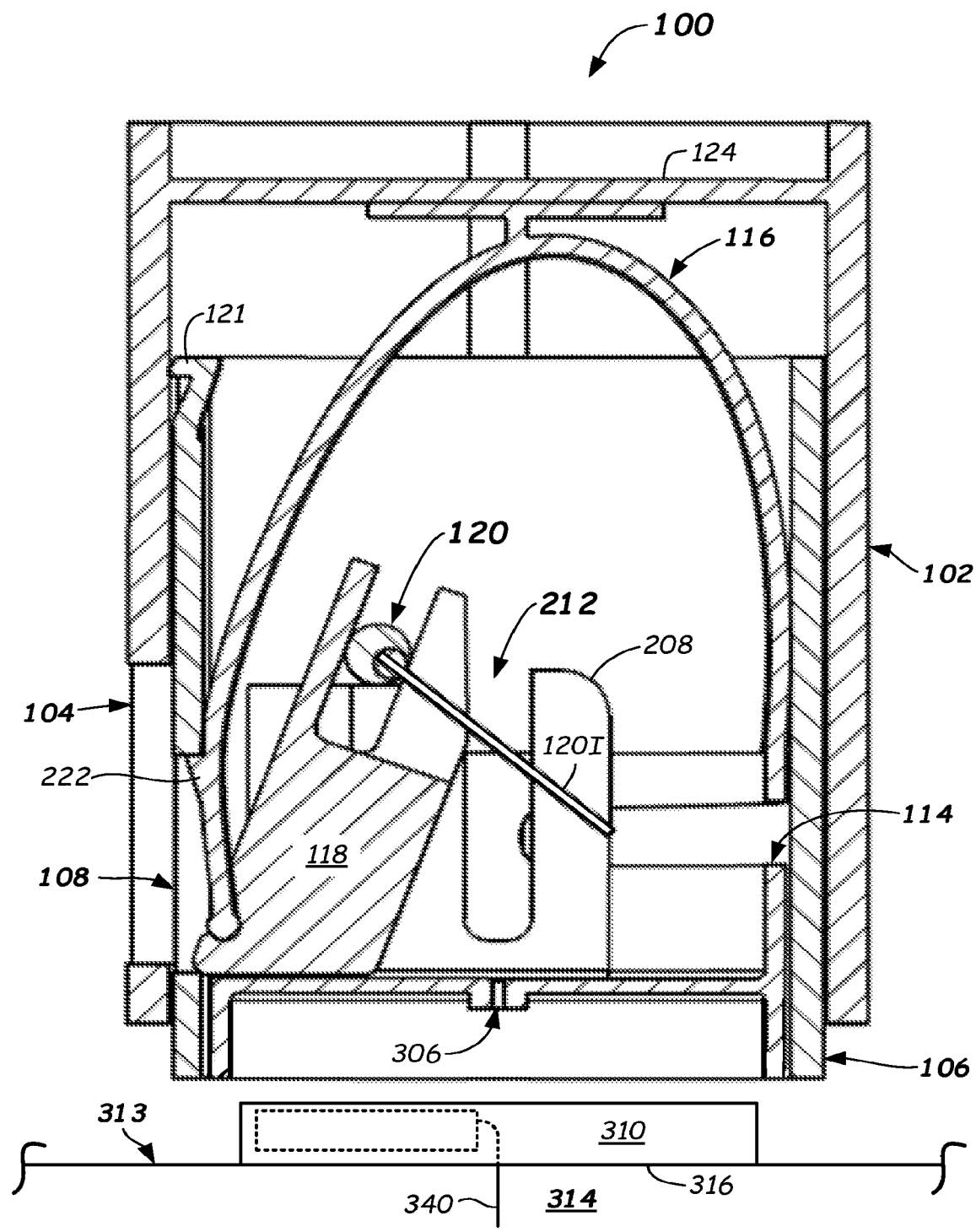

CGM inserter 100 then may be removed, leaving transmitter and biosensor assembly 310 in place, with bottom surface 316 of transmitter and biosensor assembly 310 adhered to the user's skin 313 at the insertion site 314 and biosensor 340 (e.g., a CGM or other biosensor type) implanted in contact with interstitial fluid (as shown in FIG. 3F) and coupled to the transmitter. In some embodiments, in which the outer member 102 and inner member 106 are formed of recyclable or biodegradable material, these components may be recycled or composted.

As described above, and in accordance with one or more embodiments provided herein, outer member 102 is configured to move axially relative to inner member 106. This may press bias member 116 against pivot member 118 during insertion of the biosensor 340. According to one aspect, during insertion of the biosensor 340, pivot member 118 is prevented from pivoting in a first portion of the axial stroke until after insertion when the end of the pivot member 118 passes by the upper part of the second pivot window 108 of inner member 106. Upon further axial motion between the inner member 106 and outer member 102, the first pivot window 104 of outer member 102 can sufficiently overlap with second pivot window 108 of inner member 106. This overlap in the second portion of the axial stroke allows bias member 116 to fully pivot the pivot member 118 and retract insertion device 120, which leaves the biosensor 340 implanted.

For example, during insertion of the biosensor 340, the pivot member 118 may be prevented from pivoting by contact of the end of the pivot member 118 with the inner member 106 (e.g., by guide surface 122 thereof). Furthermore, bias member 116 may include a locking feature 222 that engages second pivot window 108 of inner member 106 and restricts movement of bias member 116 and pivot member 118 after the insertion. In some embodiments, during insertion of the biosensor 340, pivot member 118 is prevented from pivoting until insertion device 120 inserts the biosensor 340 into a subcutaneous region of a user. Thereafter, the pivoting retracts the insertion device 120 leaving behind the implanted biosensor 340.

Bias member 116 may be curved within CGM inserter 100, and contact inner member 106, outer member 102, and pivot member 118 during insertion. In some embodiments, transmitter carrier 114 and bias member 116 may be formed from a single piece of material (e.g., using injection molding or a similar process) Likewise, in other embodiments, transmitter carrier 114, bias member 116, and pivot member 118 may be formed from a single piece of material (e.g., using injection molding or a similar process). Transmitter carrier 114 may include a housing (e.g., cylindrical body region 202) having a top region (e.g., upper region 204), a bottom region (e.g., lower region 206) and a recess (e.g., recess 330) or lower surface configured to support a transmitter and biosensor assembly 310 during insertion. The recess 330, if used, can be configured to include a snap-in feature adapted to retain the transmitter and biosensor assembly 310 during insertion, yet release it from the transmitter carrier 114 after insertion and retraction. In some embodiments, the housing (e.g., cylindrical body region 202) may include a compression relief feature 218 positioned between the top region 204 and bottom region 206 of the housing (e.g., cylindrical body region 202).

Figure 4:
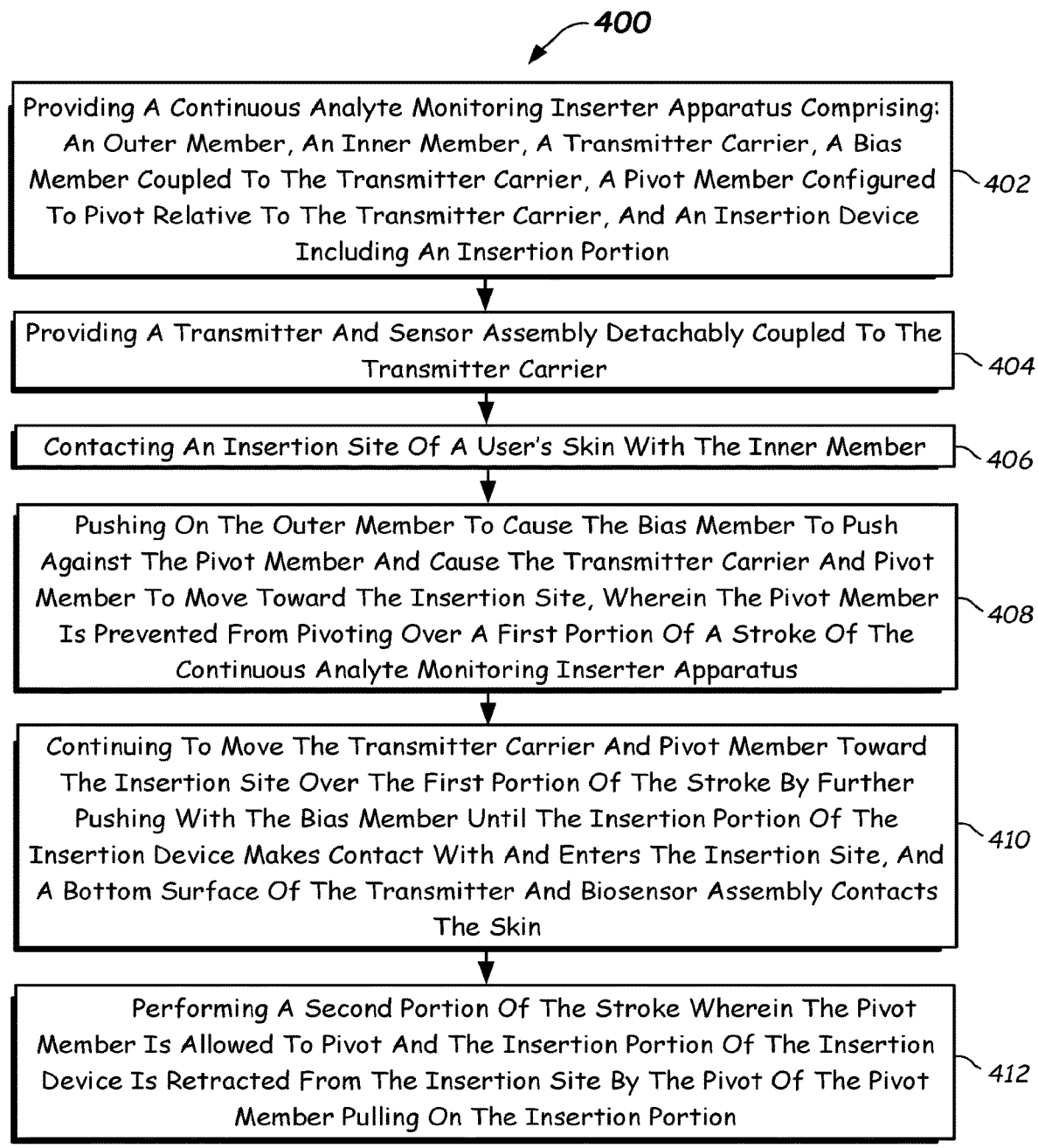
FIG. 4 illustrates a flowchart of a method of using an inserter to insert a biosensor in accordance with embodiments provided herein.
Figure 5:
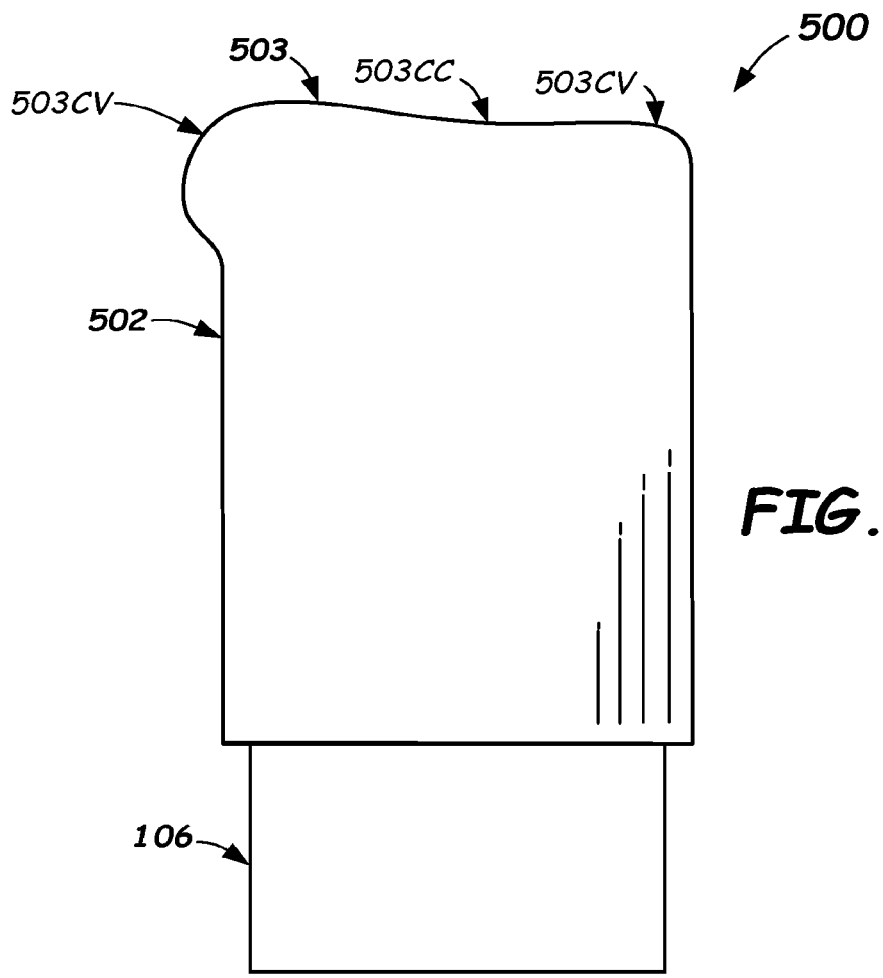
FIG. 5 is a side-perspective view of an alternative embodiment of an inserter including an ergonomic grasping portion.

Referring now to FIG. 4, an embodiment of a method 400 of using an inserter apparatus (e.g., CGM inserter 100) to insert a biosensor (e.g., CGM biosensor 340 or another biosensor type) is described. The method 400 comprises, in block 402, providing the inserter apparatus comprising: an outer member (e.g., outer member 102), which may have a first pivot window (e.g., first pivot window 104), an inner member (e.g., inner member 106), which may have a second pivot window (e.g., second pivot window 108), a transmitter carrier (e.g., transmitter carrier 114), a bias member (e.g., bias member 116), a pivot member (e.g., pivot member 118) configured to pivot relative to the transmitter carrier, and an insertion device (e.g., insertion device 120) including an insertion portion (e.g., insertion portion 1201).

The method 400 further comprises, in block 404, providing a transmitter and biosensor assembly (e.g., CGM transmitter and biosensor assembly 310) that is detachably coupled to the transmitter carrier 114. Detachably coupled means there is some suitable mechanism configured for coupling the transmitter and biosensor assembly 310 to the transmitter carrier 114 wherein the transmitter and biosensor assembly 310 can be readily detached after insertion of the biosensor (e.g., CGM biosensor 340 or another biosensor). The transmitter and biosensor assembly 310 may be mounted to the transmitter carrier 114 by any suitable mechanism facilitating the detachment thereof after insertion and retraction of the insertion device 120, such as with two or more detachment members that are released after the insertion and retraction. In some embodiments, an adhering force due to the adhesive backing adhering transmitter and biosensor assembly 310 to the user's skin can aid in the separation of the transmitter and biosensor assembly 310 from the inserter 100. Other suitable detachment mechanisms may be used.

According to the method 400, in block 406, an insertion site (e.g., insertion site 314) of a user's skin (e.g., skin 313) is contacted with the inner member (e.g., inner member 106). The insertion site (e.g., insertion site 314) is broadly a location on the user's body defining where the transmitter and biosensor assembly 310 and biosensor 340 is to be placed.

According to the method 400, in block 408, a user or other person pushes on the outer member (e.g., outer member 102) to cause the bias member (e.g., bias member 116) to push against the pivot member (e.g., pivot member 118) thus causing the transmitter carrier (e.g., transmitter carrier 114) and pivot member (e.g., pivot member 118) to move (translate) toward the insertion site (e.g., insertion site 314), wherein the pivot member is prevented from pivoting over a first portion of a stroke of the inserter 100. In the first portion of the stroke, the pivot member (e.g., pivot member 118) translates, but does not rotate or pivot.

According to the method 400, in block 410, a user or other person continues to push, thus continuing to move the transmitter carrier (e.g., transmitter carrier 114) and pivot member (e.g., pivot member 118) toward the insertion site over the first portion of the stroke by further pushing with the bias member (e.g., bias member 116) until the insertion portion (e.g., insertion portion 1201) of the insertion device (e.g., insertion device 120) makes contact with and enters the insertion site and thereby contacts interstitial fluid (under the skin), and a bottom surface (e.g., bottom surface 316) of the transmitter and biosensor assembly 310 contacts the skin 313.

According to the method 400, in block 412, in a second portion of the stroke, the pivot member (e.g., pivot member 118) is allowed to pivot and the insertion portion (e.g., insertion portion 1201) of insertion device (e.g., insertion device 120) is retracted from the insertion site (e.g., insertion site 314) by the pivot of the pivot member (e.g., pivot member 118) pulling on the insertion portion (e.g., insertion portion 1201).

According to some embodiments, the inner member comprises a pivot window (e.g., a second pivot window 108), and wherein during insertion of the biosensor (e.g., biosensor 340), the pivot member (e.g., pivot member 118) is prevented from pivoting until the pivot member enters the pivot window (e.g., second pivot window 108) of the inner member (e.g., inner member 106).

In the embodiment shown, when the first pivot window (e.g., first pivot window 104) overlaps with the second pivot window (e.g., second pivot window 108) in the second portion of the stroke, the pivot member (e.g., pivot member 118) is allowed to fully pivot (rotate) and enter into the overlapping first and second pivot windows. The retraction of the insertion portion 1201 leaves behind the biosensor 340 in contact with the interstitial fluid of the user. It should be understood that in some embodiments, a pivot window may not be needed in the outer member 102 provided that sufficient pivoting is allowed upon entering the pivot window of the inner member 106 to accomplish retraction of the insertion portion 1021.

Thus, the transmitter and biosensor assembly 310 is now positioned on the user to be able to transmit continuous analyte measurements (e.g., continuous glucose measurements) to an external receiver (not shown).

Figure 6:
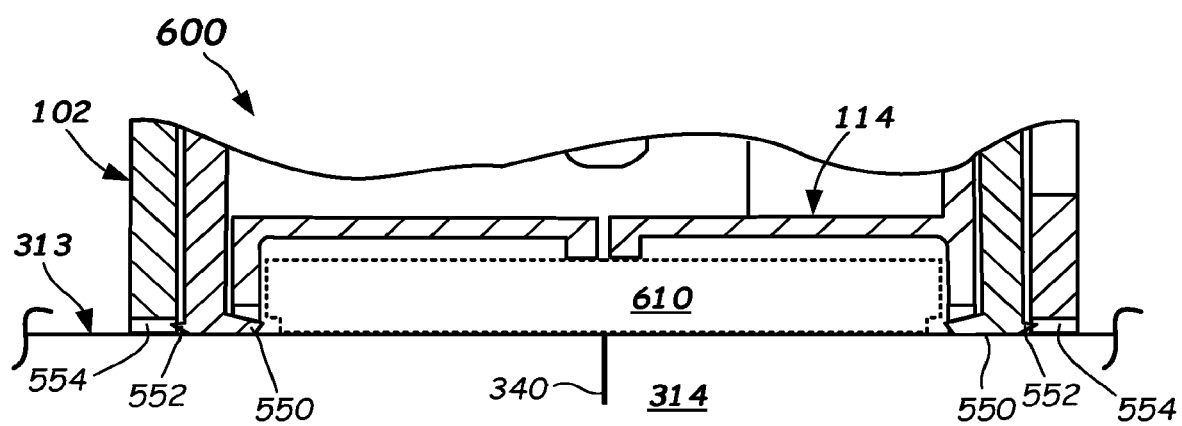
FIG. 6 is a partial cross-sectioned side view illustrating an alternative embodiment of an inserter illustrating a detachment feature enabling the detachment of the transmitter and biosensor assembly in accordance with embodiments provided herein.

One example detachment mechanism is shown in FIG. 6 embodied in a portion of an inserter apparatus 600, wherein the transmitter and biosensor assembly 610 (shown dotted) is detachably coupled to an underside of the transmitter carrier 114, in accordance with embodiments provided herein. As shown, the inner member 106 may include one or more retainer tangs 550 (two or three in some embodiments) that extend locally inward. Normally, one or more outwardly-extending, local contact features 552 on the outside surface of the inner member 106 are in contact with the inside surface of the outer member 102, which thereby bends portions of the inner member 106 locally and moves the retainer tangs 550 inward to retain and hold the transmitter and biosensor assembly 610. Upon the outer member 102 being pushed far enough towards the user's skin (as shown), one or more local relief openings 554 align with the one or more local contact features 552 so that the local contact features 552 are allowed to snap back into the one or more local relief openings 554. This causes retainer tangs 550 to move away from, and free, the transmitter and biosensor assembly 610 so that it can be separated from the inserter apparatus 600.

Figure 7:
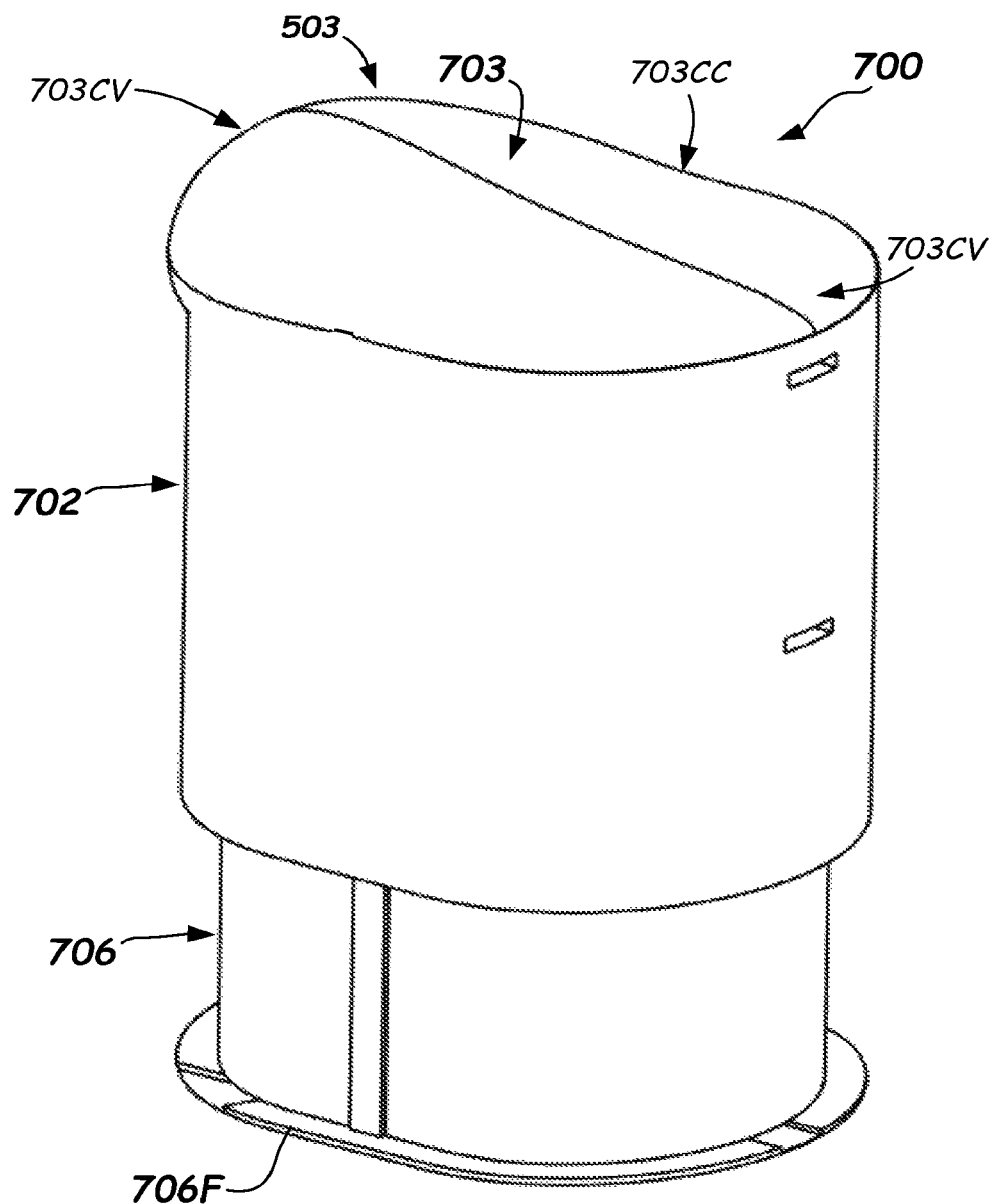
FIG. 7 is a perspective side view of an alternative embodiment of an inserter including oval outer cross-sections in accordance with embodiments provided herein.

FIG. 7 illustrates an alternative embodiment of an inserter apparatus 700. In this embodiment, the outer member 702 and inner member 706 each include an oval outer shape in cross-section in accordance with embodiments provided herein. Likewise, the outer member 702 includes a top profile 703 including a non-planar surface profile including convex curved surface portions 702CV and possibly some concave curved surface portions 702CC. Inner member 706 may include a lower flange 706F extending at least part way or fully around the lower circumference to help stabilize the inserter apparatus 700.

Figure 8A:
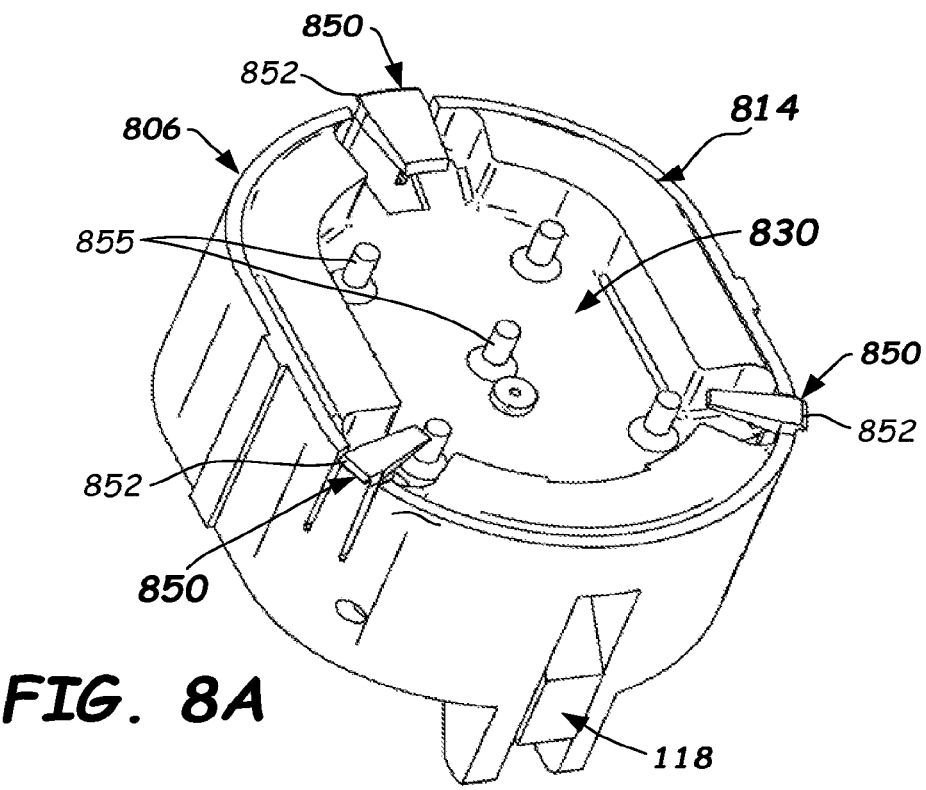
FIG. 8A is a perspective bottom view of a transmitter carrier of an inserter of FIG. 7 in accordance with embodiments provided herein.
Figure 8B:
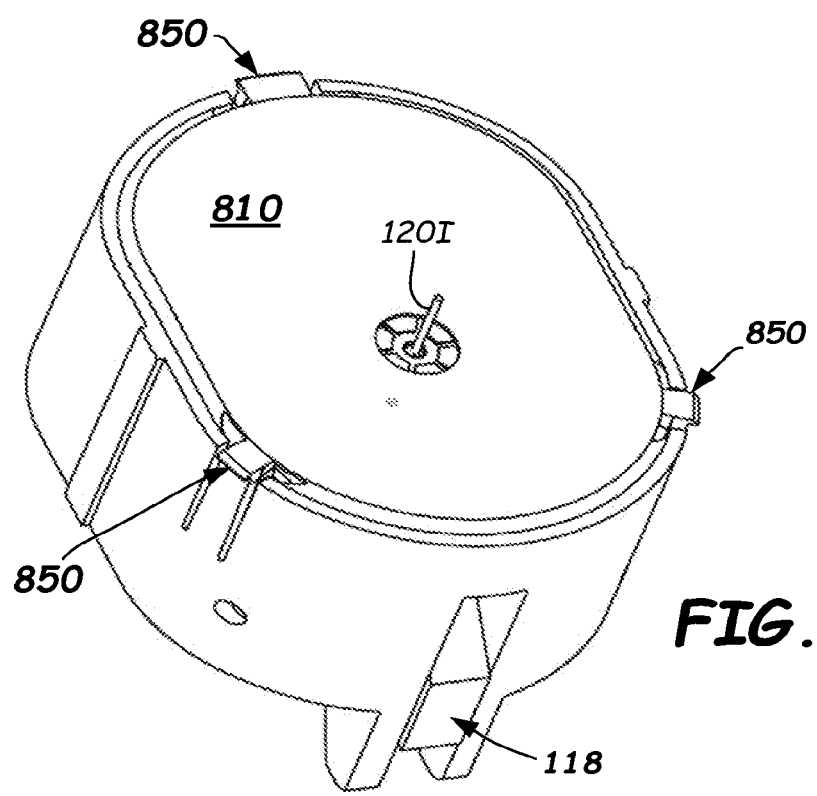
FIG. 8B is a perspective bottom view of a transmitter carrier having mounted therein a transmitter and biosensor assembly in accordance with embodiments provided herein.

FIGS. 8A and 8B illustrate perspective bottom views of an inner member 806 and transmitter carrier 814 that can be used in an inserter apparatus similar to that shown in FIG. 7 in accordance with embodiments provided herein. The transmitter carrier 814 includes a pivot member 118 and insertion device including insertion portion 1201 that may be configured as previously described herein. The insertion portion 1201 is configured to extend through the transmitter and biosensor assembly 810. Multiple retainer tangs 850 (like retainer tangs 550) move inward normally to retain and hold the transmitter and biosensor assembly 810 in recess 830 as the inner member 806 is received in outer member (not shown). As the transmitter carrier 814 is pushed far enough within inner member 806 to the position shown, local contact features 852 are allowed to snap back into the one or more local relief openings (like local relief openings 554) and thus retainer tangs 850 can move away from, and free, the transmitter and biosensor assembly 810 so that it can be separated from the inserter apparatus 800. As shown, recess 830 may include one or more alignment pins 855 (a few labeled) that interface with holes (not shown) in the top surface of the transmitter and biosensor assembly 810 to align the transmitter and biosensor assembly 810 with the transmitter carrier 814.

The foregoing description discloses only example embodiments. Modifications of the above-disclosed apparatus and methods, which fall within the scope of this disclosure, will be readily apparent to those of ordinary skill in the art. For example, the shape of the CGM inserter 100 is shown as cylindrical. However, other outer member and inner member shapes such as oval, oblong, or other shaped cross-sections may be used.

The invention claimed is:

1. A continuous analyte monitoring inserter apparatus, comprising:
   an outer member comprising a first pivot window;
   an inner member configured to slidably fit axially within the outer member, the inner member comprising a second pivot window;
   a transmitter carrier comprising a bias member, wherein the transmitter carrier is configured to support a transmitter and biosensor assembly within the inner member;
   an insertion device; and
   a pivot member configured to pivot relative to the transmitter carrier and support the insertion device,
      wherein axial movement of the outer member is configured to slide over the inner member and press the bias member against an end of the pivot member,
      wherein over a first portion of a stroke, the bias member causes the pivot member to impart the axial movement to the transmitter carrier and the insertion device,
      wherein over a second portion of the stroke, the pivot member pivots to retract the insertion device when the end of the pivot member passes through an opening created by an overlapping of the first pivot window with the second pivot window, and
      wherein upon completion of the second portion of the stroke, a locking feature of the bias member is configured to engage with the second pivot window to prevent the bias member from retracting, thereby preventing the pivot member from pivoting after insertion of a biosensor.

2. The continuous analyte monitoring inserter apparatus of claim 1, wherein the outer member includes a first alignment feature, and the inner member includes a second alignment feature, wherein the first alignment feature is configured to interface with the second alignment feature to vertically align the first pivot window of the outer member with the second pivot window of the inner member.

3. The continuous analyte monitoring inserter apparatus of claim 1, wherein the axial movement of the pivot member over the first portion of the stroke facilitates the insertion of the biosensor, and wherein a pivot motion of the pivot member over the second portion of the stroke facilitates retraction of the insertion device.

4. The continuous analyte monitoring inserter apparatus of claim 3, wherein during the insertion of the biosensor, the pivot member is prevented from pivoting until the pivot member enters the second pivot window of the inner member.

5. The continuous analyte monitoring inserter apparatus of claim 1, wherein the transmitter carrier is configured to support the transmitter and biosensor assembly during the insertion of the biosensor of the transmitter and biosensor assembly.

6. The continuous analyte monitoring inserter apparatus of claim 1, wherein the pivot member includes an insertion device support feature configured to support the insertion device during the insertion of the biosensor.

7. The continuous analyte monitoring inserter apparatus of claim 1, wherein the pivot member includes a bias member interface feature configured to interface with the bias member.

8. The continuous analyte monitoring inserter apparatus of claim 1, wherein the bias member is curved within the continuous analyte monitoring inserter apparatus.

9. The continuous analyte monitoring inserter apparatus of claim 8, wherein during the insertion, the bias member contacts the inner member, the outer member, and the pivot member.

10. The continuous analyte monitoring inserter apparatus of claim 1, wherein at least the transmitter carrier and the bias member are formed from a single piece of material.

11. The continuous analyte monitoring inserter apparatus of claim 1, wherein the transmitter carrier includes a housing having a top region, and a bottom region configured to support the transmitter and biosensor assembly during the insertion.

12. The continuous analyte monitoring inserter apparatus of claim 11, wherein the housing includes a compression relief feature positioned between the top region and the bottom region of the housing.

13. The continuous analyte monitoring inserter apparatus of claim 1, wherein the inner member includes a pre-insertion lock feature configured to extend into the first pivot window of the outer member so as to prevent the outer member from sliding over the inner member prior to the insertion.

14. The continuous analyte monitoring inserter apparatus of claim 1, wherein the bias member is flexible.

15. The continuous analyte monitoring inserter apparatus of claim 1, wherein the outer member and the inner member each include an oval outer shape in cross-section.

16. The continuous analyte monitoring inserter apparatus of claim 1, wherein the inner member includes one or more retainer tangs that extend locally inward to retain and hold the transmitter and biosensor assembly, and wherein the outer member comprises one or more local relief openings and the inner member comprises one or more local contact features, and the one or more local contact features are allowed to snap into the one or more local relief openings allowing the one or more retainer tangs to move away from and free the transmitter and biosensor assembly.

17. A method of forming an inserter apparatus, comprising:
    assembling a transmitter carrier assembly;
    inserting the transmitter carrier assembly into an inner member, the inner member comprising an inner member-pivot window and an inner member-alignment feature; and
    inserting the inner member into an outer member, the outer member comprising an outer member-pivot window and an outer member-alignment feature;
    wherein the transmitter carrier assembly comprises:
        an insertion device;
        a bias member comprising an end feature and a locking feature;
        a pivot member, comprising:
            an insertion device support feature configured to support the insertion device, and
            a bias member interface feature configured to couple with the end feature of the bias member; and
        a transmitter carrier comprising a supporting structure defining a guide region configured to support the pivot member;
    wherein assembling the transmitter carrier assembly comprises:
        placing the insertion device into the insertion device support feature of the pivot member and into the guide region of the transmitter carrier; and
        bending the bias member so that the end feature of the bias member contacts the bias member interface feature of the pivot member; and
    wherein, when assembled, axial motion of the outer member relative to the inner member presses the end feature of the bias member against the pivot member,
        wherein over a first portion of a stroke, the end feature of the bias member causes the pivot member to impart axial movement to the transmitter carrier and the insertion device,
        wherein over a second portion of the stroke, the pivot member pivots to retract the insertion device when an end of the pivot member passes through an opening created by an overlapping of the outer member-pivot window with the inner member-pivot window,
        wherein upon completion of the second portion of the stroke, the locking feature of the bias member is configured to engage with the inner member-pivot window to prevent the bias member from retracting, thereby preventing the pivot member from pivoting after insertion of a biosensor.

18. A method of inserting a biosensor, the method comprising:
    placing an inserter apparatus in contact with an insertion site, wherein the inserter apparatus comprises:
        an outer member,
        an inner member,
        a transmitter carrier,
        a bias member coupled to the transmitter carrier,
        a pivot member configured to pivot relative to the transmitter carrier, and
        an insertion device comprising an insertion portion;
        wherein a transmitter and biosensor assembly is detachably coupled to the transmitter carrier, the transmitter and biosensor assembly comprising a transmitter and the biosensor;
    pushing on the outer member to cause the bias member to push against the pivot member thus causing the transmitter carrier and the pivot member to move toward the insertion site, wherein the pivot member is prevented from pivoting over a first portion of a stroke of the inserter apparatus;
    continuing to move the transmitter carrier and the pivot member toward the insertion site over the first portion of the stroke by further pushing with the bias member until the insertion portion of the insertion device contacts and enters the insertion site and contacts interstitial fluid and a bottom surface of the transmitter and biosensor assembly contacts the insertion site, the insertion portion of the insertion device thereby inserting the biosensor at the insertion site contacting the biosensor with the interstitial fluid; and
    performing a second portion of the stroke, wherein the pivot member exhibits a pivot motion, the pivot motion causing the pivot member to pull on the insertion device, and wherein the pivot member pulling on the insertion device retracts the insertion portion of the insertion device from the insertion site with the biosensor remaining inserted at the insertion site and contacting the interstitial fluid;
    wherein the outer member comprises a first pivot window and the inner member comprises a second pivot window,
    wherein at least a portion of the pivot motion of the pivot member occurs with the first pivot window of the outer member overlapping the second pivot window of the inner member,
    wherein during the pivot motion, an end portion of the pivot member enters the first pivot window by way of the second pivot window, and
    wherein upon completion of the second portion of the stroke, a locking feature of the bias member is configured to engage with the second pivot window to prevent the bias member from retracting, thereby preventing the pivot member from pivoting after insertion of the biosensor.

19. The method of claim 18 wherein during the insertion of the biosensor, the pivot member is prevented from pivoting until the pivot member enters the second pivot window of the inner member.

20. The method of claim 18 wherein the pivot member is allowed to fully pivot when the first pivot window overlaps with the second pivot window.

* * * * *